(12) United States Patent
Mahadevan-Jansen et al.

(10) Patent No.: US 10,325,366 B2
(45) Date of Patent: Jun. 18, 2019

(54) METHODS AND SYSTEMS FOR THREE-DIMENSIONAL REAL-TIME INTRAOPERATIVE SURGICAL MARGIN EVALUATION OF TUMOR TISSUES

(71) Applicant: VANDERBILT UNIVERSITY, Nashville, TN (US)

(72) Inventors: Anita Mahadevan-Jansen, Nashville, TN (US); The-Quyen Nguyen, Evanston, IL (US); Xiaohong Bi, Nashville, TN (US); Zain Gowani, Nashville, TN (US); Ginger Holt, Nashville, TN (US); Isaac Pence, Crestwood, KY (US); John Nguyen, Pomona, CA (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/730,996

(22) Filed: Oct. 12, 2017

(65) Prior Publication Data

US 2018/0053298 A1 Feb. 22, 2018

Related U.S. Application Data

(62) Division of application No. 14/085,732, filed on Nov. 20, 2013, now Pat. No. 9,824,440.

(Continued)

(51) Int. Cl.
*G06T 7/00* (2017.01)
*G01N 21/64* (2006.01)
*G01N 21/65* (2006.01)
*A61B 5/00* (2006.01)

(52) U.S. Cl.
CPC .......... *G06T 7/0012* (2013.01); *A61B 5/0071* (2013.01); *A61B 5/0075* (2013.01);
(Continued)

(58) Field of Classification Search
CPC ............... G01N 21/6486; G01N 21/65; G01N 2021/656; G01N 21/64; G01N 2201/0846;
(Continued)

(56) References Cited

U.S. PATENT DOCUMENTS

| 6,485,413 B1 * | 11/2002 | Boppart | A61B 1/00096 356/450 |
| 2007/0167836 A1 * | 7/2007 | Scepanovic | A61B 5/0071 600/476 |

(Continued)

*Primary Examiner* — Kenny A Cese
(74) *Attorney, Agent, or Firm* — Locke Lord LLP; Tim Tingkang Xia, Esq.

(57) ABSTRACT

A method of evaluating a surgical margin of tumor tissues of a living subject includes acquiring images of a specimen of the tumor tissues; calculating a three-dimensional (3D) morphological surface of the specimen from the acquired images and displaying the 3D morphological surface; obtaining, from the 3D morphological surface, a plurality of specimen locations to cover a surface of the specimen; acquiring optical data at each specimen location; evaluating a margin status of the specimen at each specimen location to either positive or negative based on the acquired optical data; and displaying the margin status of the specimen on the 3D morphological surface of the specimen with morphological orientations.

15 Claims, 17 Drawing Sheets

Related U.S. Application Data

(60) Provisional application No. 61/728,346, filed on Nov. 20, 2012, provisional application No. 61/821,442, filed on May 9, 2013.

(52) U.S. Cl.
CPC ...... *A61B 2505/05* (2013.01); *G01N 21/6486* (2013.01); *G01N 21/65* (2013.01); *G01N 2201/0846* (2013.01); *G06T 2207/30096* (2013.01)

(58) Field of Classification Search
CPC ........ G06T 2207/30096; G06T 7/0012; A61K 49/0017; G01B 11/2441; G01B 2290/65; G02B 27/4227; G02B 5/1828; A61B 5/0075; A61B 5/0066; A61B 5/0071; A61B 2505/05
See application file for complete search history.

(56) References Cited

U.S. PATENT DOCUMENTS

| | | | |
|---|---|---|---|
| 2008/0039742 A1* | 2/2008 | Hashinnshony | A61B 5/0071 600/587 |
| 2009/0326384 A1* | 12/2009 | Bigio | A61B 5/0075 600/476 |
| 2012/0123205 A1* | 5/2012 | Nie | A61B 1/00174 600/109 |

* cited by examiner

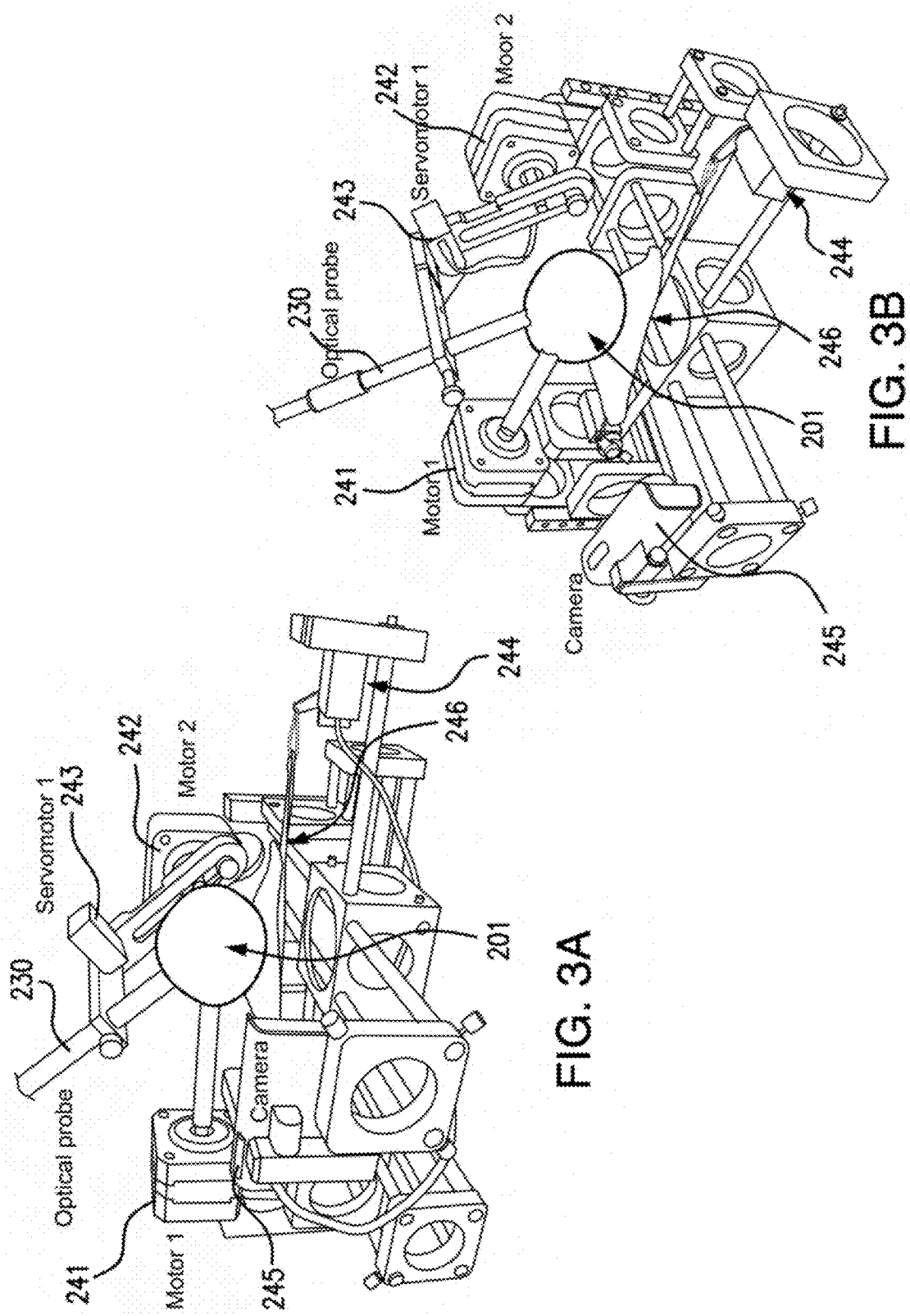

METHODS AND SYSTEMS FOR THREE-DIMENSIONAL REAL-TIME INTRAOPERATIVE SURGICAL MARGIN EVALUATION OF TUMOR TISSUES

CROSS-REFERENCE TO RELATED PATENT APPLICATIONS

This application is a divisional application of U.S. patent application Ser. No. 14/085,732, filed Nov. 20, 2013, entitled "METHODS AND SYSTEMS FOR THREE-DIMENSIONAL REAL-TIME INTRAOPERATIVE SURGICAL MARGIN EVALUATION OF TUMOR TISSUES," by Anita Mahadevan-Jansen et al., now allowed, which itself claims priority to and the benefit of, pursuant to 35 U.S.C. § 119(e), U.S. provisional patent application Ser. No. 61/728,346, filed Nov. 20, 2012, entitled "METHODS AND SYSTEMS FOR 3D, REAL TIME AND INTRAOPERATIVE SURGICAL MARGIN EVALUATION," by The Quyen Nguyen et al., and U.S. provisional patent application Ser. No. 61/821,442, field May 9, 2013, entitled "SYSTEMS AND METHODS FOR TUMOR BED ASSESSMENT," by The Quyen Nguyen et al., which are incorporated herein in their entireties by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [21] represents the 21st reference cited in the reference list, namely, Mahadevan-Jansen, A. in *Raman Spectroscopy: From Benchtop to Bedside, Biomedical Photonics Handbook*, (ed 30:1-30:27 T. Vo-Dinh, CRC Press, Washington D.C., 2003.).

STATEMENT AS TO RIGHTS UNDER FEDERALLY-SPONSORED RESEARCH

This invention was made with government support under grant number W81XWH 09-1-0037 awarded by the Department of Defense Breast Cancer Research Program. The government has certain rights in the invention.

FIELD OF THE INVENTION

The present invention relates generally to surgical procedures, and more particularly to methods and systems for evaluating surgical margins of tumor tissues of a living subject and a non-transitory computer-readable medium storing instructions which, when executed by a processor, cause the system to perform the method for evaluating the surgical margin of the specimen.

BACKGROUND OF THE INVENTION

Soft tissue sarcomas (STS) are a heterogeneous group of malignant tumors that arise from mesenchymal tissues including fibrous connective tissue, cartilage, blood vessels, muscles, nerves, or fat. In the United States, it is estimated that some 11,280 new cases were diagnosed, and 3900 patients died of STS in the year 2012 [1]. The mainstay of local treatment is to completely excise the tumor with a margin of normal tissue so that no malignant cells remain in the tumor bed. The presence of residual sarcoma cells in the tumor bed is associated with local recurrence, which reduces patient survival rates [2-4]. For patients with residual tumor cells at the margin of the resected tumor, re-excision and/or postoperative radiation is required. Such additional therapies increase patient morbidity and healthcare costs.

It has been shown that the presence of cancer cells within the margin of resected specimens is strongly correlated with the risk of local tumor recurrence. Margins therefore play a key role in the prognosis of patients with respect to local recurrence and are directly correlated to the success of surgeries. Consequently, there is a need for intraoperative evaluation of the resection front so that immediate re-excision of suspicious margins can be performed.

Resected specimens differ in shape, size and firmness. Depending on the size and stage of the tumor, the resected specimen can vary in shape and size. The firmness of resected specimen is sometime related to age and body mass index of the patient. This variation in size, sharp and firmness makes the measurement of the specimen surface difficult.

In addition, there is no universal definition of a safe margin (i.e., the thickness of healthy tissue surrounding the tumor). Depending on the organ's location, the size of the safe surgical margin is defined differently. In fact, 2 mm is the safe margin widely accepted by breast surgeons. But most urological surgeons will define the safe margin as the absence of tumor at the surface of the removed prostate specimen. Accordingly, the safe margin should be no more than 0.05 mm in this case.

Generally, any method used to evaluate the surgical margins of a resected specimen must be precise, rapid and relatively simple to implement in order to be used in routine clinical care. The method should be able to scan the entire surface of specimens despite their differences in shape and size; and measure the sample surface while leaving it intact, thus minimizing the physical change of the margin status due to pressure. Furthermore, the method should be able to be applied for a wide range of surgery types for example breast, skin, and prostate cancer surgeries. Besides a precise diagnose of margin status, the method should also provide exact locations of the positive margin (if any are found) in a manner that the surgeon can easily recognize and correctly remove more tissues.

Therefore, a heretofore unaddressed need exists in the art to address the aforementioned deficiencies and inadequacies.

SUMMARY OF THE INVENTION

One aspect of the present invention relates to a method of evaluating a surgical margin of tumor tissues of a living subject, which includes: (a) acquiring images of a specimen of the tumor tissues; (b) calculating a three-dimensional (3D) morphological surface of the specimen from the acquired images and displaying the 3D morphological surface; (c) obtaining, from the 3D morphological surface, a plurality of specimen locations to cover a surface of the specimen; (d) acquiring optical data at each specimen location; (e) evaluating a margin status of the specimen at each specimen location to either positive or negative based on the acquired optical data; and (f) displaying the margin status of the specimen on the 3D morphological surface of the specimen with morphological orientations.

In certain embodiments, the step of acquiring the optical data includes: providing a source light; delivering the source light at each specimen location onto a surface of the specimen; and collecting diffused/reflected light generated from interaction of the source light with the specimen at the specimen location.

In certain embodiments, the step of acquiring the optical data is performed with at least one optical probe or at least one detector.

In certain embodiments, each optical probe includes a plurality of optical fibers spatially arranged in a fiber array. In certain embodiments, for each optical probe, the optical fibers include a source fiber for delivering the source light emitted from the light source to the surface of the specimen, and a plurality of collection fibers for collecting the diffused/reflected light generated from the interaction of the source light with the specimen. In certain embodiments, the source fiber is positioned in a center of the fiber array, and the plurality of collection fibers is positioned in one or more rings having a center at the source fiber such that each collection fiber is offset from the source fiber.

In certain embodiments, the method further includes cooperatively moving the specimen and the at least one optical probe to acquire the optical data at all of the specimen locations.

In certain embodiments, the method further includes: mounting the specimen in a scanner; and calibrating a position of the specimen in the scanner. In certain embodiments, the scanner includes: a sample holder for holding the specimen; a first motor for rotating the specimen along a first horizontal axis; and a second motor for moving the at least one optical probe along a surface of the specimen. In certain embodiments, the scanner further includes a camera for acquiring images of the specimen so as to reconstruct a three-dimensional (3D) morphological surface of the specimen.

In certain embodiments, the evaluating step includes: generating a fluorescence signal from the images acquired by the camera; and determining the margin status according to the fluorescence signal.

In certain embodiments, the evaluating step includes: obtaining a raw spectrum from the optical data; generating a Raman spectrum (RS) from the raw spectrum; and determining the margin status according to the RS.

In certain embodiments, the evaluating step includes: obtaining a raw spectrum from the optical data; generating a fluorescence spectrum (FS) and a Raman spectrum (RS) from the raw spectrum; and determining the margin status according to the FS and the RS.

In certain embodiments, the plurality of collection optical fibers is divided into N groups, such that a first group of the collection optical fibers each is positioned away along a radial direction from the source optical fiber with a first spatial offset $R_1$, and a N-th group of the collection optical fibers each is positioned away along the radial direction from the source optical fiber with a N-th spatial offset $R_N$, where N is an positive integer, and $R_1 \leq R_2 \leq \ldots \leq R_{N-1} \leq R_N$. In one embodiment, the tumor tissues include breast cancer tissues, N=3, $R_1$=1.57 mm, $R_2$=2.68 mm, and $R_3$=3.50 mm. In one embodiment, the evaluating step includes: determining the margin status using a spatially offset Raman spectroscopy (SORS) from the optical data.

In one embodiment, the evaluating step includes: obtaining a raw spectrum from the optical data; generating a fluorescence spectrum (FS) from the raw spectrum; and determining the margin status according to the FS.

In another aspect, the present invention relates to a system for evaluating a surgical margin of tumor tissues of a living subject. In one embodiment, the system includes: (a) a light source configured to emit a source light; (b) at least one optical probe coupled with the light source, each of the at least one optical probe has a working end, a source channel and a plurality of collection channels, wherein when the working end is positioned proximate to a surface of a specimen of the tumor tissues, the source channel is configured to deliver the source light emitted by the light source from the working end to the surface of the specimen, and the collection channels are configured to collect from the working end diffused/reflected light generated from interaction of the source light with the specimen; (c) a scanner coupled with the at least one optical probe, configured to cooperatively move the specimen and the at least one optical probe so as to probe a plurality of specimen locations, wherein the specimen locations cover the surface of the specimen; (d) a detector coupled with the at least one optical probe, configured to receive the collected diffused/reflected light to evaluate a margin status of the specimen; and (e) a controller coupled with the scanner and the detector, configured to operably control the scanner and the detector.

In certain embodiments, each optical probe includes a plurality of optical fibers spatially arranged in a fiber array. In certain embodiments, for each optical probe, the optical fibers include a source fiber for delivering the source light emitted from the light source to the surface of the specimen, and a plurality of collection fibers for collecting the diffused/reflected light generated from the interaction of the source light with the specimen. In certain embodiments, the source fiber is positioned in a center of the fiber array, and the plurality of collection fibers is positioned in one or more rings having a center at the source fiber such that each collection fiber is offset from the source fiber.

In certain embodiments, the detector includes a spectrometer. In certain embodiments, the detector includes a charge-coupled device (CCD).

In certain embodiments, the detector is configured to: generate optical data from the received collected diffused/reflected light; obtain a raw spectrum from the optical data; generate a fluorescence spectrum (FS) and a Raman spectrum (RS) from the raw spectrum; and determine the margin status according to the FS and the RS.

In certain embodiments, the scanner includes: a sample holder for holding the specimen; a first motor for rotating the specimen along a first horizontal axis; and a second motor for moving the at least one optical probe along a surface of the specimen. In certain embodiments, the scanner further includes a camera for acquiring images of the specimen so as to reconstruct a three-dimensional (3D) morphological surface of the specimen.

In certain embodiments, the detector is configured to: obtain a raw spectrum from the optical data; generate a Raman spectrum (RS) from the raw spectrum; and determine the margin status according to the RS.

In certain embodiments, the detector is configured to: generate a fluorescence signal from the images acquired by the camera; and determine the margin status according to the fluorescence signal.

In certain embodiments, the detector is configured to: generate optical data from the received collected diffused/reflected light; obtain a raw spectrum from the optical data; generate a Raman spectrum (RS) from the raw spectrum; generate a fluorescence image (FI) from the images acquired by the camera; and determine the margin status according to the FI and the RS.

In certain embodiments, the controller includes a computer. In certain embodiments, the computer has a display for displaying the 3D morphological surface and displaying the margin status of the specimen in the 3D morphological surface with morphological orientations.

In certain embodiments, the plurality of collection optical fibers is divided into N groups, such that a first group of the collection optical fibers each is positioned away along a radial direction from the source optical fiber with a first spatial offset $R_1$, and a N-th group of the collection optical fibers each is positioned away along the radial direction from the source optical fiber with a N-th spatial offset $R_N$, where N is an positive integer, and $R_1 \leq R_2 \leq \ldots \leq R_{N-1} \leq R_N$. In one embodiment, the tumor tissues include breast cancer tissues, N=3, $R_1$=1.57 mm, $R_2$=2.68 mm, and $R_3$=3.50 mm. In one embodiment, the detector is configured to: generate the optical data from the collected diffused/reflected light; obtain a raw spectrum from the optical data collected by each of the N groups of the collection optical fibers; generate a Raman spectrum (RS) from the raw spectrum collected by each of the N groups of the collection optical fiber; and determine the margin status according to the RS collected by each of the N groups of the collection optical fiber.

In one embodiment, the detector is configured to: generate optical data from the received collected diffused/reflected light; obtain a raw spectrum from the optical data; generate a fluorescence spectrum (FS) from the raw spectrum; and determine the margin status according to the FS.

A further aspect of the present invention relates to a non-transitory computer-readable medium storing computer executable instructions which, when executed by a processor, cause a system to perform a method for evaluating a surgical margin of tumor tissues of a living subject. In certain embodiments, the method includes: (a) acquiring images of a specimen of the tumor tissues; (b) calculating a three-dimensional (3D) morphological surface of the specimen from the acquired images and displaying the 3D morphological surface; (c) obtaining, from the 3D morphological surface, a plurality of specimen locations to cover a surface of the specimen; (d) acquiring optical data at each specimen location; (e) evaluating a margin status of the specimen at each specimen location to either positive or negative based on the acquired optical data; and (f) displaying the margin status of the specimen on the 3D morphological surface of the specimen with morphological orientations.

In certain embodiments, the step of acquiring the optical data includes: providing a source light; delivering the source light at each specimen location onto the surface of the specimen; collecting diffused/reflected light generated from interaction of the source light with the specimen at the specimen location; and evaluate the margin status of the specimen from the collected diffused/reflected light at each specimen location of the surface of the specimen.

In certain embodiments, the step of acquiring the optical data is performed with at least one optical probe or at least one detector.

In certain embodiments, the method further includes cooperatively moving the specimen and the at least one optical probe to acquire the optical data at all of the specimen locations.

In certain embodiments, the evaluating step includes: obtaining a raw spectrum from the optical data; generating a fluorescence spectrum (FS) and a Raman spectrum (RS) from the raw spectrum; and determining the margin status according to the FS and the RS.

In certain embodiments, the method further includes: mounting the specimen in a scanner; and calibrating a position of the specimen in the scanner. In certain embodiments, the scanner includes a camera for acquiring images of the specimen so as to reconstruct a three-dimensional (3D) morphological surface of the specimen.

In certain embodiments, the evaluating step includes: obtaining a raw spectrum from the optical data; generating a Raman spectrum (RS) from the raw spectrum; and determining the margin status according to the RS.

In certain embodiments, the evaluating step includes: generating a fluorescence signal from the images acquired by the camera; and determining the margin status according to the fluorescence signal.

In certain embodiments, the evaluating step includes: obtaining a raw spectrum from the optical data; generating a Raman spectrum (RS) from the raw spectrum; generating a fluorescence image (FI) from the images acquired by the camera; and determining the margin status according to the FI and the RS.

In certain embodiments, the at least one optical probe includes: (a) a source optical fiber; and (b) a plurality of collection optical fibers arranged in an array, wherein the plurality of collection optical fibers is divided into N groups, such that a first group of the collection optical fibers each is positioned away along a radial direction from the source optical fiber with a first spatial offset $R_1$, and a N-th group of the collection optical fibers each is positioned away along the radial direction from the source optical fiber with a N-th spatial offset $R_N$, where N is an positive integer, and $R_1 \leq R_2 \leq \ldots \leq R_{N-1} \leq R_N$. In one embodiment, the tumor tissues include breast cancer tissues, N=3, $R_1$=1.57 mm, $R_2$=2.68 mm, and $R_3$=3.50 mm. In one embodiment, the evaluating step includes: generating the optical data from the collected diffused/reflected light; obtaining a raw spectrum from the optical data collected by each of the N groups of the collection optical fibers; generating a Raman spectrum (RS) from the raw spectrum collected by each of the N groups of the collection optical fiber; and determining the margin status according to the RS collected by each of the N groups of the collection optical fiber.

In one embodiment, the evaluating step includes: obtaining a raw spectrum from the optical data; generating a fluorescence spectrum (FS) from the raw spectrum; and determining the margin status according to the FS.

In another aspect, the present invention relates to a method of evaluating a surgical margin of tumor tissues of a living subject. In one embodiment, the method includes: (a) reconstructing a three-dimensional (3D) morphological surface of a specimen of the tumor tissues; (b) automatically acquiring optical data at a plurality of specimen locations on a surface of the specimen, wherein the specimen locations cover a surface of the specimen; (c) automatically evaluating a margin status of the specimen based on the acquired optical data at each specimen location on the surface of the specimen; and (d) displaying the margin status of the specimen on the 3D morphological surface of the specimen with morphological orientations.

In certain embodiments, the reconstructing step includes: acquiring images of the specimen; and reconstructing the three-dimensional (3D) morphological surface of the specimen based on the acquired images of the specimen.

In certain embodiments, the acquiring step includes: providing a source light; delivering the source light at each specimen location onto the surface of the specimen; and collecting diffused/reflected light generated from interaction of the source light with the specimen at the specimen location.

In certain embodiments, the acquiring step is performed with at least one optical probe or at least one detector, and wherein each optical probe comprises a plurality of optical fibers spatially arranged in a fiber array. In certain embodiments, for each optical probe, the optical fibers include a source fiber for delivering the source light emitted from the light source to the surface of the specimen, and a plurality of collection fibers for collecting the diffused/reflected light generated from the interaction of the source light with the specimen. In certain embodiments, the source fiber is positioned in a center of the fiber array, and the plurality of collection fibers is positioned in one or more rings having a center at the source fiber such that each collection fiber is offset from the source fiber.

In certain embodiments, the evaluating step includes: obtaining a raw spectrum from the optical data; generating a fluorescence spectrum (FS) and a Raman spectrum (RS) from the raw spectrum; and determining the margin status according to the FS and the RS.

In certain embodiments, the method further includes: calculating the specimen locations to cover the surface of the specimen.

In certain embodiments, the method further includes: mounting the specimen in a scanner; and calibrating a position of the specimen in the scanner. In certain embodiments, the scanner includes: a sample holder for holding the specimen; a first motor for rotating the specimen along a first horizontal axis; and a second motor for moving the at least one optical probe along a surface of the specimen. In certain embodiments, the scanner further includes a camera for acquiring images of the specimen so as to reconstruct a three-dimensional (3D) morphological surface of the specimen.

In certain embodiments, the evaluating step includes: obtaining a raw spectrum from the optical data; generating a Raman spectrum (RS) from the raw spectrum; and determining the margin status according to the RS.

In certain embodiments, the evaluating step includes: generating a fluorescence signal from the images acquired by the camera; and determining the margin status according to the fluorescence signal.

In certain embodiments, the evaluating step includes: obtaining a raw spectrum from the optical data; generating a Raman spectrum (RS) from the raw spectrum; generating a fluorescence image (FI) from the images acquired by the camera; and determining the margin status according to the FI and the RS.

In certain embodiments, the plurality of collection optical fibers is divided into N groups, such that a first group of the collection optical fibers each is positioned away along a radial direction from the source optical fiber with a first spatial offset $R_1$, and a N-th group of the collection optical fibers each is positioned away along the radial direction from the source optical fiber with a N-th spatial offset $R_N$, where N is an positive integer, and $R_1 \leq R_2 \leq \ldots \leq R_{N-1} \leq R_N$. In one embodiment, the tumor tissues include breast cancer tissues, N=3, $R_1$=1.57 mm, $R_2$=2.68 mm, and $R_3$=3.50 mm. In one embodiment, the evaluating step includes: generating the optical data from the collected diffused/reflected light; obtaining a raw spectrum from the optical data collected by each of the N groups of the collection optical fibers; generating a Raman spectrum (RS) from the raw spectrum collected by each of the N groups of the collection optical fiber; and determining the margin status according to the RS collected by each of the N groups of the collection optical fiber.

In one embodiment, the evaluating step includes: obtaining a raw spectrum from the optical data; generating a fluorescence spectrum (FS) from the raw spectrum; and determining the margin status according to the FS.

In yet another aspect, a system for evaluating a surgical margin of tumor tissues of a living subject includes: (a) a reconstruction device configured to reconstruct a three-dimensional (3D) morphological surface of a specimen of the tumor tissues; (b) an acquiring device configured to acquiring optical data at a plurality of specimen locations, wherein the specimen locations cover a surface of the specimen; (c) an evaluating device configured to evaluate a margin status of the specimen based on the acquired optical data at each specimen location on the surface of the specimen; (d) a display device configured to display the 3D morphological surface and to display the margin status of the specimen on the 3D morphological surface of the specimen with morphological orientations.

In certain embodiments, the acquiring device includes: a light source configured to emit a source light; at least one optical probe coupled with the light source, each of the at least one optical probe has a working end, a source channel and a plurality of collection channels, wherein when the working end is positioned proximate to a surface of a specimen of the tumor tissues, the source channel is configured to deliver the source light emitted by the light source from the working end to the surface of the specimen, and the collection channels are configured to collect from the working end diffused/reflected light generated from interaction of the source light with the specimen; and a scanner coupled with the at least one optical probe, configured to cooperatively move the specimen and the at least one optical probe so as to probe each of the specimen locations.

In certain embodiments, each optical probe includes a plurality of optical fibers spatially arranged in a fiber array. In certain embodiments, for each optical probe, the optical fibers include a source fiber for delivering the source light emitted from the light source to the surface of the specimen, and a plurality of collection fibers for collecting the diffused/reflected light generated from the interaction of the source light with the specimen. In certain embodiments, the source fiber is positioned in a center of the fiber array, and the plurality of collection fibers is positioned in one or more rings having a center at the source fiber such that each collection fiber is offset from the source fiber.

In certain embodiments, the scanner includes: a sample holder for holding the specimen; a first motor for rotating the specimen along a first horizontal axis; and a second motor for moving the at least one optical probe along the surface of the specimen.

In certain embodiments, the evaluating device includes a detector coupled to the at least one optical probe, configured to receive the collected diffused/reflected light to evaluate the margin status of the specimen.

In certain embodiments, the detector is configured to: generate optical data from the received collected diffused/reflected light; obtain a raw spectrum from the optical data; generate a fluorescence spectrum (FS) and a Raman spectrum (RS) from the raw spectrum; and determine the margin status according to the FS and the RS.

In certain embodiments, the reconstruction device includes: a camera for acquiring images of the specimen;

and a processor for reconstructing the 3D morphological surface of the specimen based on the acquired images of the specimen.

In certain embodiments, the detector is configured to: obtain a raw spectrum from the optical data; generate a Raman spectrum (RS) from the raw spectrum; and determine the margin status according to the RS.

In certain embodiments, the detector is configured to: generate a fluorescence signal from the images acquired by the camera; and determine the margin status according to the fluorescence signal.

In certain embodiments, the detector is configured to: generate optical data from the received collected diffused/reflected light; obtain a raw spectrum from the optical data; generate a Raman spectrum (RS) from the raw spectrum; generate a fluorescence image (FI) from the images acquired by the camera; and determine the margin status according to the FI and the RS.

In certain embodiments, the plurality of collection optical fibers is divided into N groups, such that a first group of the collection optical fibers each is positioned away along a radial direction from the source optical fiber with a first spatial offset $R_1$, and a N-th group of the collection optical fibers each is positioned away along the radial direction from the source optical fiber with a N-th spatial offset $R_N$, where N is an positive integer, and $R_1 \leq R_2 \leq \ldots \leq R_{N-1} \leq R_N$. In one embodiment, the tumor tissues include breast cancer tissues, N=3, $R_1$=1.57 mm, $R_2$=2.68 mm, and $R_3$=3.50 mm. In one embodiment, the detector is configured to: generate the optical data from the collected diffused/reflected light; obtain a raw spectrum from the optical data collected by each of the N groups of the collection optical fibers; generate a Raman spectrum (RS) from the raw spectrum collected by each of the N groups of the collection optical fiber; and determine the margin status according to the RS collected by each of the N groups of the collection optical fiber.

In one embodiment, the detector is configured to: generate optical data from the received collected diffused/reflected light; obtain a raw spectrum from the optical data; generate a fluorescence spectrum (FS) from the raw spectrum; and determine the margin status according to the FS.

In a further aspect, the present invention relates to a non-transitory computer-readable medium storing instructions which, when executed by a processor, cause a system to perform a method of evaluating a surgical margin of tumor tissues of a living subject. In one embodiment, the method includes: (a) reconstructing a three-dimensional (3D) morphological surface of a specimen of the tumor tissues; (b) automatically acquiring optical data at a plurality of specimen locations on a surface of the specimen, wherein the specimen locations cover a surface of the specimen; (c) automatically evaluating a margin status of the specimen based on the acquired optical data at each specimen location on the surface of the specimen; and (d) displaying the margin status of the specimen on the 3D morphological surface of the specimen with morphological orientations.

In certain embodiments, the reconstructing step includes: acquiring images of the specimen; and reconstructing the three-dimensional (3D) morphological surface of the specimen based on the acquired images of the specimen.

In certain embodiments, the acquiring step includes: providing a source light; delivering the source light at each specimen location onto the surface of the specimen; and collecting diffused/reflected light generated from interaction of the source light with the specimen at the specimen location.

In certain embodiments, the acquiring step is performed with at least one optical probe or at least one detector, and each optical probe includes a plurality of optical fibers spatially arranged in a fiber array. In certain embodiments, for each optical probe, the optical fibers include a source fiber for delivering the source light emitted from the light source to the surface of the specimen, and a plurality of collection fibers for collecting the diffused/reflected light generated from the interaction of the source light with the specimen. In certain embodiments, the source fiber is positioned in a center of the fiber array, and the plurality of collection fibers is positioned in one or more rings having a center at the source fiber such that each collection fiber is offset from the source fiber.

In certain embodiments, the method further includes cooperatively moving the specimen and the at least one optical probe to acquire the optical data at all of the specimen locations.

In certain embodiments, the evaluating step includes: obtaining a raw spectrum from the optical data; generating a fluorescence spectrum (FS) and a Raman spectrum (RS) from the raw spectrum; and determining the margin status according to the FS and the RS.

In certain embodiments, the method further includes: calculating the specimen locations to cover the surface of the specimen.

In certain embodiments, the method further includes: mounting the specimen in a scanner; and calibrating a position of the specimen in the scanner. In certain embodiments, the scanner includes a camera for acquiring images of the specimen so as to reconstruct a three-dimensional (3D) morphological surface of the specimen.

In certain embodiments, the evaluating step includes: obtaining a raw spectrum from the optical data; generating a Raman spectrum (RS) from the raw spectrum; and determining the margin status according to the RS.

In certain embodiments, the evaluating step includes: generating a fluorescence signal from the images acquired by the camera; and determining the margin status according to the fluorescence signal.

In certain embodiments, the evaluating step includes: obtaining a raw spectrum from the optical data; generating a Raman spectrum (RS) from the raw spectrum; generating a fluorescence image (FI) from the images acquired by the camera; and determining the margin status according to the FI and the RS.

In a further aspect, the present invention relates to an optical probe for evaluating boundary of tumor tissues of a living subject. In one embodiment, the optical probe includes: (a) a source optical fiber; and (b) a plurality of collection optical fibers arranged in an array, wherein the plurality of collection optical fibers is divided into N groups, such that a first group of the collection optical fibers each is positioned away along a radial direction from the source optical fiber with a first spatial offset $R_1$, and a N-th group of the collection optical fibers each is positioned away along the radial direction from the source optical fiber with a N-th spatial offset $R_N$, where N is an positive integer, and $R_1 \leq R_2 \leq \ldots \leq R_{N-1} \leq R_N$.

In certain embodiments, the source optical fiber is positioned in a center of the optical probe, and each of the N groups of the collection optical fibers is positioned in a ring having a center at the source optical fiber such that each of the collection optical fibers in the N-th group is offset from the source optical fiber with the N-th spatial offset $R_N$. In one embodiment, the tumor tissues include breast cancer tissues, N=3, $R_1$=1.57 mm, $R_2$=2.68 mm, and $R_3$=3.50 mm.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIGS. 3A and 3B show schematically two views of a system for evaluating a surgical margin of a specimen of a living subject according to certain embodiments of the present invention.

DETAILED DESCRIPTION OF THE INVENTION

Figure 1:
FIG. 1 shows a typical tumor bed after the STS excision according to certain embodiments of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "plurality" means two or more.

As used herein, the terms "comprising", "including", "carrying", "having", "containing", "involving", and the like are to be understood to be open-ended, i.e., to mean including but not limited to.

The term "tissues" or "tumor tissues," as used herein, refers to a collection of cells of a living subject (e.g., a human being or other animals). In certain embodiments, the tissues may include tissues in or on the body of the living subject, and/or tissues resected from the body of the living subject.

The term "specimen" of the tissues, as used herein, refers to samples of body tissues. The specimen of the tissues may be scanned or processed on site (i.e., in or on the body of the living subject), or may be resected from the body for scanning and processing purposes.

Overview of the Invention

The present invention relates to methods and systems for evaluating surgical margins of tumor tissues of a living subject and a non-transitory computer-readable medium storing instructions which, when executed by a processor, cause the system to perform the method for evaluating the surgical margin of the specimen.

Resected specimens differ in shape, size and firmness. Depending on the size and stage of the tumor, the resected specimen can vary in shape and size. The firmness of resected specimen is sometime related to age and body mass index of the patient. This variation in size, sharp and firmness makes the measurement of the specimen surface difficult.

In addition, there is no universal definition of a safe margin (i.e., the thickness of healthy tissue surrounding the tumor). Depending on the organ's location, the size of the safe surgical margin is defined differently. In fact, 2 mm is the safe margin widely accepted by breast surgeons. But most urological surgeons will define the safe margin as the absence of tumor at the surface of the removed prostate specimen. Accordingly, the safe margin should be no more than 0.05 mm in this case.

Generally, any method used to evaluate the surgical margins of a resected specimen must be precise, rapid and relatively simple to implement in order to be used in routine clinical care. The method should be able to scan the entire surface of specimens despite their differences in shape and size; and measure the sample surface while leaving it intact, thus minimizing the physical change of the margin status due to pressure. Furthermore, the method should be able to be applied for a wide range of surgery types for example breast, skin, and prostate cancer surgeries. Besides a precise diagnose of margin status, the method should also provide exact locations of the positive margin (if any are found) in a manner that the surgeon can easily recognize and correctly remove more tissues.

As described above, a method used to evaluate the surgical margins of a resected specimen has the follow three requirements:

(a) Precise diagnose of margin status: the method should have a high sensitivity and specificity in evaluating the margin. The device should measure the sample surface while leaving it intact, thus minimizing the physical change of the margin status due to pressure, which will limit the false positive diagnosis.

(b) Rapid diagnosis and simple to implement in routine clinical care: the method should perform automatic measurement, without human intervention, and the total measurement time must be less than 20 minutes so that the measurement does not interfere with the surgery plan. The device should be able to automatically scan the entire surface of the sample and provide exact locations of the positive margin (if any are found) in a manner that the surgeon can easily recognize and correctly remove more tissues.

(c) Different margin size configuration: the margin size can vary from several microns to several millimeters for different margin size applications.

Current intraoperative margin assessment methods have limitations. Frozen sections are commonly used but are time consuming and prone to sampling error [5] especially with large tumor beds. For example, FIG. 1 shows a typical tumor bed after the STS excision according to certain embodiments of the present invention. As shown in FIG. 1, the rectangles marked the biopsied locations for frozen section pathology. Magnetic resonance imaging (MRI) provides general evaluation of the extent of tumor and thus allows for image-guided surgery, but has limited sensitivity [6]. Serial sectioning of the resected tumor with standard histopathology provides a definitive diagnosis of margin status, but results may take from several days to over a week.

Limitations in current methods therefore highlight the need for a rapid, accurate, automated guidance tool that can be used in the operating room during tumor resection so that immediate re-excision of suspicious margins can be performed, minimizing the necessity for a second surgery and its associated risks. This would significantly improve the management of the STS disease regarding both time and cost. It will cost $6,000-$10,000 for re-excision surgery and postoperative radiation; those additional procedures, following incomplete tumor removal, increase morbidity rates and cause significant physical, emotional, mental, and economic stress for patients.

In the present disclosure, we propose a solution using source light to evaluate the surgical margin. In certain embodiments, the system utilizes optical devices to detect the presence of any microscopic residual sarcoma cells in the tumor bed, report their locations to surgeons so that more tissue can be removed, and thus help to ensure complete removal of the tumor with clear margins in a single procedure. The system would solve a critical problem in STS care by greatly reducing or eliminating the need for re-operation/radiation as well as reducing the time, cost, and anxiety associated with repeat surgeries and additional radiations One aspect of the present invention relates to a method of evaluating a surgical margin of tumor tissues of a living subject, which includes: (a) acquiring images of a specimen of the tumor tissues; (b) calculating a three-dimensional (3D) morphological surface of the specimen from the acquired images and displaying the 3D morphological surface; (c) obtaining, from the 3D morphological surface, a plurality of specimen locations to cover a surface of the specimen; (d) acquiring optical data at each specimen location; (e) evaluating a margin status of the specimen at each specimen location to either positive or negative based on the acquired optical data; and (f) displaying the margin status of the specimen on the 3D morphological surface of the specimen with morphological orientations.

In another aspect, the present invention relates to a system for evaluating a surgical margin of tumor tissues of a living subject. In one embodiment, the system includes: (a) a light source configured to emit a source light; (b) at least one optical probe coupled with the light source, each of the at least one optical probe has a working end, a source channel and a plurality of collection channels, wherein when the working end is positioned proximate to a surface of a specimen of the tumor tissues, the source channel is configured to deliver the source light emitted by the light source from the working end to the surface of the specimen, and the collection channels are configured to collect from the working end diffused/reflected light generated from interaction of the source light with the specimen; (c) a scanner coupled with the at least one optical probe, configured to cooperatively move the specimen and the at least one optical probe so as to probe a plurality of specimen locations, wherein the specimen locations cover the surface of the specimen; (d) a detector coupled with the at least one optical probe, configured to receive the collected diffused/reflected light to evaluate a margin status of the specimen; and (e) a controller coupled with the scanner and the detector, configured to operably control the scanner and the detector.

A further aspect of the present invention relates to a non-transitory computer-readable medium storing computer executable instructions which, when executed by a processor, cause a system to perform a method for evaluating a surgical margin of tumor tissues of a living subject. In certain embodiments, the method includes: (a) acquiring images of a specimen of the tumor tissues; (b) calculating a three-dimensional (3D) morphological surface of the specimen from the acquired images and displaying the 3D morphological surface; (c) obtaining, from the 3D morphological surface, a plurality of specimen locations to cover a surface of the specimen; (d) acquiring optical data at each specimen location; (e) evaluating a margin status of the specimen at each specimen location to either positive or negative based on the acquired optical data; and (f) displaying the margin status of the specimen on the 3D morphological surface of the specimen with morphological orientations.

In another aspect, the present invention relates to a method of evaluating a surgical margin of tumor tissues of a living subject. In one embodiment, the method includes: (a) reconstructing a three-dimensional (3D) morphological surface of a specimen of the tumor tissues; (b) automatically acquiring optical data at a plurality of specimen locations on a surface of the specimen, wherein the specimen locations cover a surface of the specimen; (c) automatically evaluating a margin status of the specimen based on the acquired optical data at each specimen location on the surface of the specimen; and (d) displaying the margin status of the specimen on the 3D morphological surface of the specimen with morphological orientations.

In yet another aspect, a system for evaluating a surgical margin of tumor tissues of a living subject includes: (a) a reconstruction device configured to reconstruct a three-dimensional (3D) morphological surface of a specimen of the tumor tissues; (b) an acquiring device configured to acquiring optical data at a plurality of specimen locations, wherein the specimen locations cover a surface of the specimen; (c) an evaluating device configured to evaluate a margin status of the specimen based on the acquired optical data at each specimen location on the surface of the specimen; (d) a display device configured to display the 3D morphological surface and to display the margin status of the specimen on the 3D morphological surface of the specimen with morphological orientations.

In a further aspect, the present invention relates to a non-transitory computer-readable medium storing instructions which, when executed by a processor, cause a system to perform a method of evaluating a surgical margin of tumor tissues of a living subject. In one embodiment, the method includes: (a) reconstructing a three-dimensional (3D) morphological surface of a specimen of the tumor tissues; (b) automatically acquiring optical data at a plurality of specimen locations on a surface of the specimen, wherein the specimen locations cover a surface of the specimen; (c) automatically evaluating a margin status of the specimen based on the acquired optical data at each specimen location on the surface of the specimen; and (d) displaying the margin status of the specimen on the 3D morphological surface of the specimen with morphological orientations.

In certain embodiments, the non-transitory tangible computer-readable storage medium includes, but not limited to, disk, CD-ROM, read-only memory (ROM), random memory (RAM), flash dive, or the likes.

These and other aspects of the present invention are more specifically described below.

Implementations and Examples of the Invention

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

One aspect of the present invention relates to a system for evaluating a surgical margin of tumor tissues of a living subject. In certain embodiments, the system is capable of measuring the entire surface of a specimen in real time, and can perform at least the following tasks:

(1) reconstructing the 3D morphology of the specimen;
(2) automatically measuring the entire surface of the specimen;
(3) automatically evaluating the surgical margin status based on the presence of a cancer signal in optical signal recorded at each location; and
(4) displaying the surgical margin status in 3D with morphological orientations of the specimen.

Further, the system provides new solutions and fulfills the three requirements:

Precise: The system measures the margin status while leaving the sample intact. Very little/no pressure will be put on the sample surface. The risk of false positive margin due to surface deformation is thus minimized. Combining with high sensitivity and specificity in the margin evaluation of the optical technique, the system thus gives rise to precise diagnosis of the margin status.

Rapid and simple: As the 3D morphology of the sample is known, the entire surface of the sample can be automatically scanned. The margin status of the entire specimen can be automatically evaluated without human intervention.

Various margin sizes: As the system can be used with different optical techniques, it can be used in different margin size settings. In fact, different optical techniques have different depth resolutions which can range from several microns to several millimeters. By selecting an appropriate optical technique, one can obtain an appropriate depth resolution for a specific margin application.

Figure 2A:
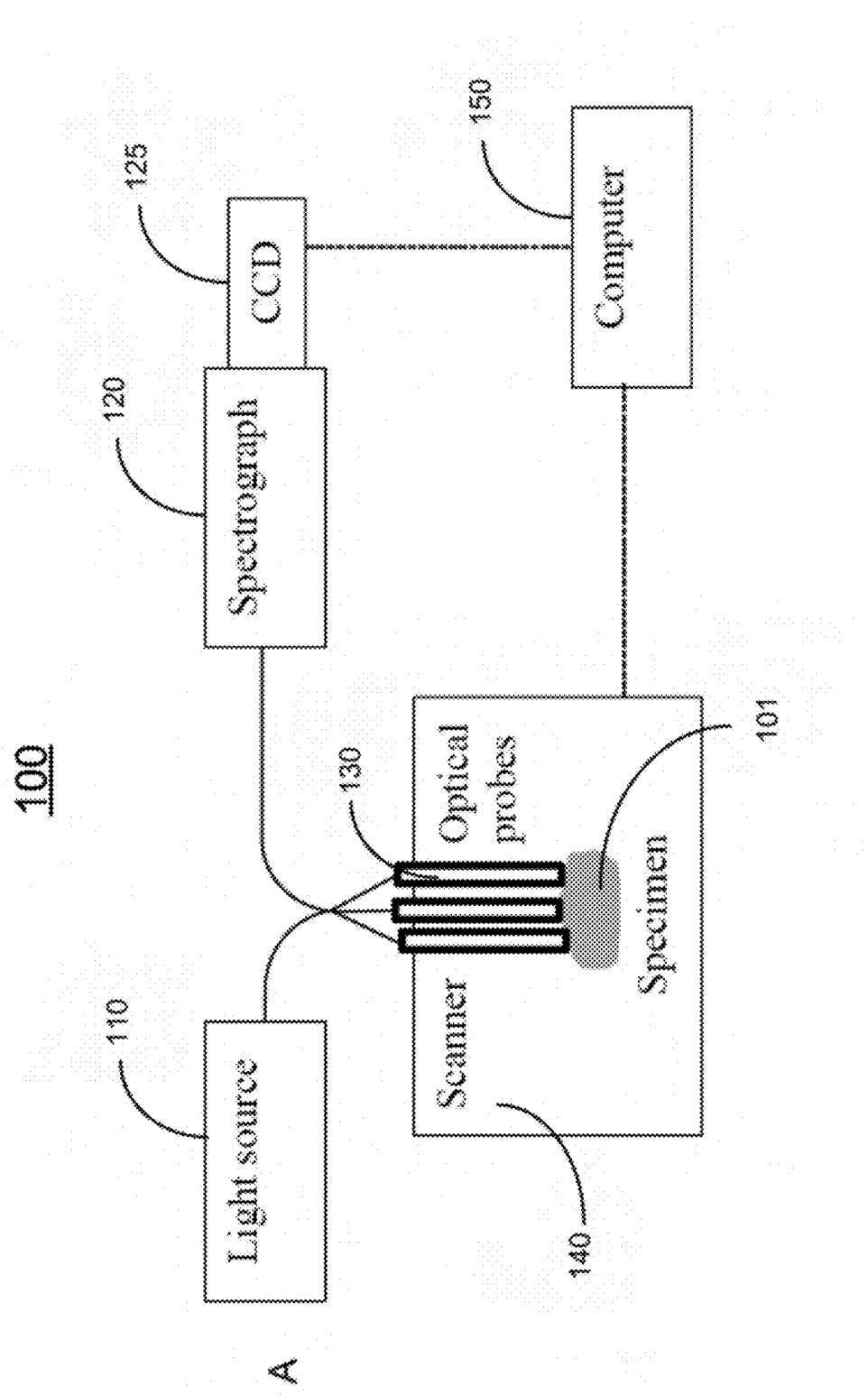
FIG. 2A shows schematically a system for evaluating a surgical margin of tumor tissues of a living subject according to certain embodiments of the present invention.

FIG. 2A shows schematically a system for evaluating a surgical margin of tumor tissues of a living subject according to certain embodiments of the present invention. Referring to FIG. 2A, the system 100 includes a light source 110, a spectrometer 120 with a detector, for example, a charge-coupled device (CCD) 125, multiples optical probes 130 and a scanner 140. A computer 150 is used to control the scanner 140 and the spectrometer 120.

The light source 110 is configured to emit a source light. The optical probes 130 are coupled with the light source 110. Each of the at least one optical probe has a working end, a source channel and a plurality of collection channels, which will be described later.

The computer 150 serves as a controller of the system 100. In certain embodiments, the computer 150 may include a display for displaying the 3D morphological surface and displaying the margin status of the specimen in the 3D morphological surface with morphological orientations.

Figure 2B:
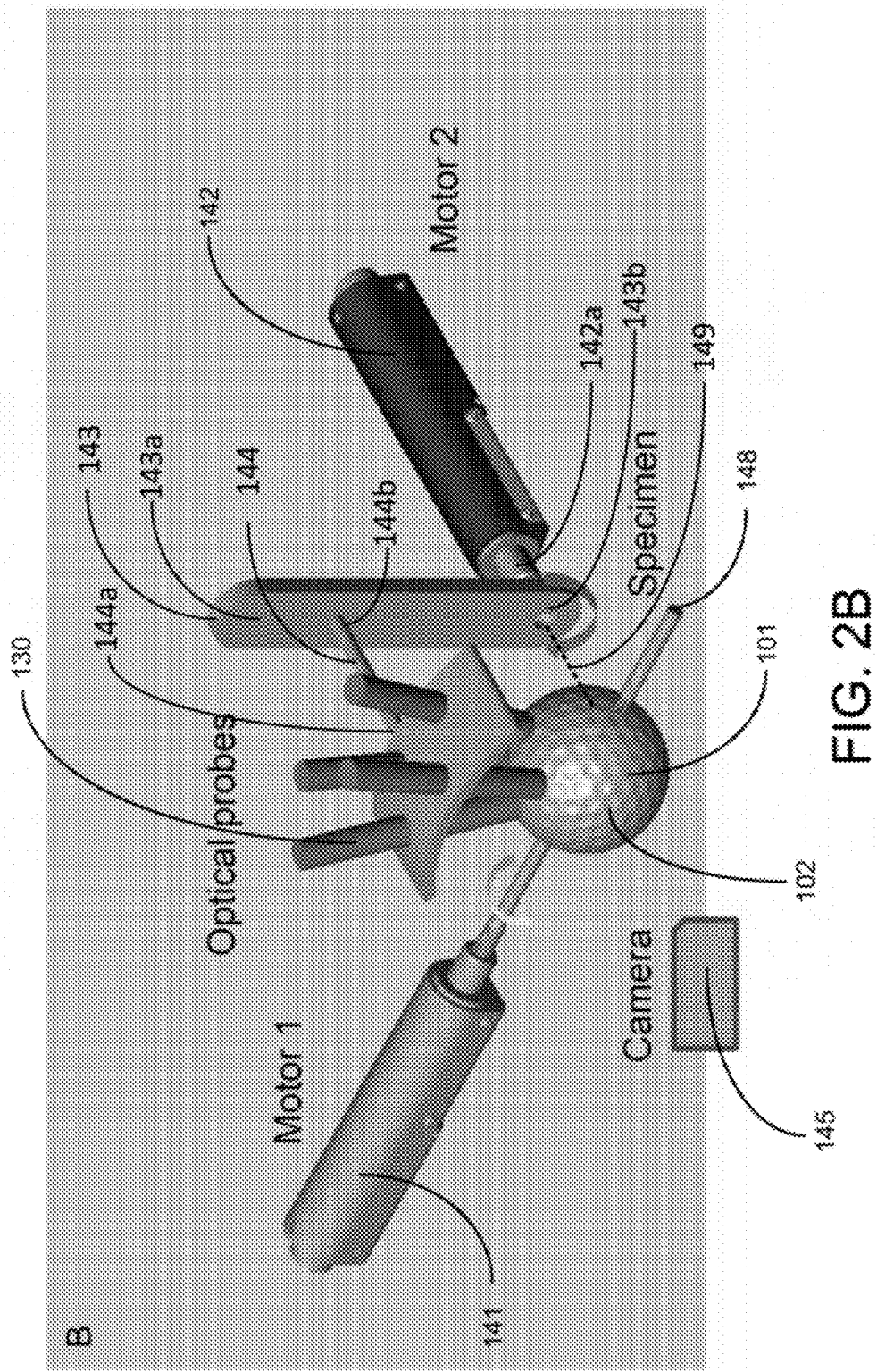
FIG. 2B shows schematically a scanner utilized in the system as shown in FIG. 2A according to certain embodiments of the present invention.

FIG. 2B shows schematically a scanner utilized in the system as shown in FIG. 2A according to certain embodiments of the present invention. As shown in FIG. 2B, the scanner 140 includes two motors 141 and 142, a probe holder (143, 144), and a camera 145. The probe holder has a first member 143 having a first end portion 143a and an opposite, second end portion 143b, and a second member 144 having a first end portion 144a and an opposite, second end portion 144b. The first and second end portions 144a and 144b of the second member 144 are respectively connected to the at least one optical probe 130 (e.g., four optical probes shown in FIG. 2B according to one embodiment of the invention) and the first end portion 143a of the first member 143 such that the first member 143 and the second member 144 are perpendicular to each other. The use of four optical probes 130 mounted on the probe holder of the scanner 140 is demonstrated. The optical probes 130 have a working end (i.e., the bottom end) placed proximal to the surface 102 of the specimen 101. The first motor 141 operably rotates the specimen 101 around its horizontal axis 148. The second motor 142 has an output shaft 142a extending along a second horizontal axis 149 that has an angle relative to the first horizontal axis 148. The angle between the first and second horizontal axes 148 and 149 is greater than zero. In the exemplary embodiment shown in FIG. 2B, the first and second horizontal axes 148 and 149 is substantially perpendicular to each other. The output shaft 142a is connected to the second end portion 143b of the first member 143 of the probe holder such that the output shaft 142a is perpendicular to the first member 143. The output shaft 142a of the second motor 142 operably rotates around the second horizontal axis 149, rotation of the output shaft 142a of the second motor 142 drives the first and second members 143 and 144 of the probe holder to rotate around the second horizontal axis 149, which in turn drives the at least one optical probe 130 to rotate around the second horizontal axis 149. As such arrangement, in operation, the first motor 141 rotates the specimen 101 around the first horizontal axis 148, while the second motor 142 rotates the optical probes 130 over the surface 102 of the specimen 101 around the second horizontal axis 149, so that a plurality of specimen locations on the surface of the specimen 101 can be probed. When the light source 110 emits the source light, the optical probes 130 receive the source light from the light source 110, and deliver the source light from the working end onto the surface 102 of the specimen 101. The source light will then interact with the surface 102 of the specimen 101 and generate diffused/reflected light. The optical probes 130 then collect from the working end the diffused/reflected light generated from interaction of the source light with the specimen 101, and send the collected diffused/reflected light to the spectrometer 120. The collected diffused/reflected light is used to evaluate the margin status of the specimen 101. The camera 145 captures images of the specimen 101, and the images are used to reconstruct the 3D morphology of the specimen 101.

Figure 2C:
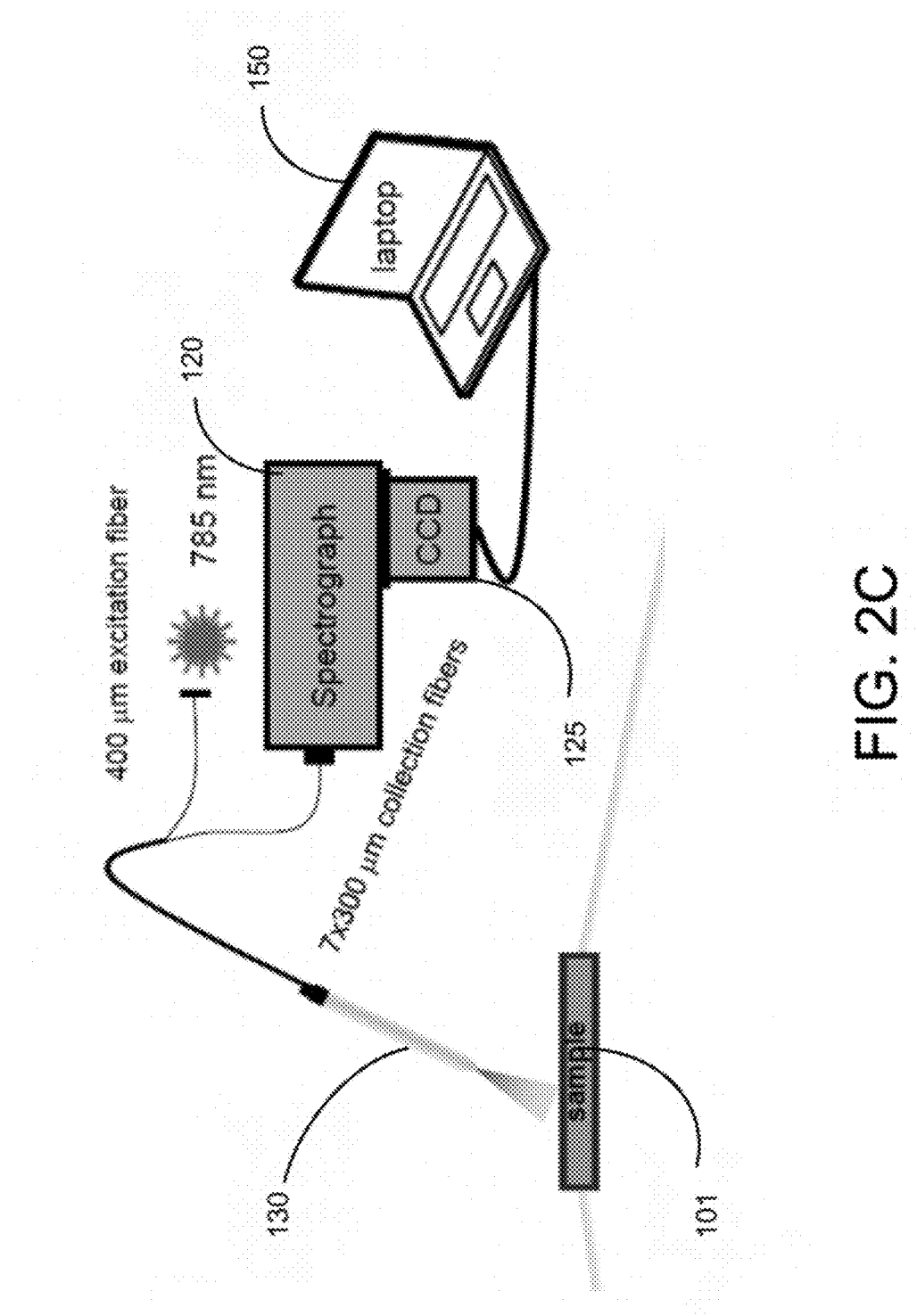
FIG. 2C shows schematically a system for evaluating a surgical margin of tumor tissues of a living subject according to certain embodiments of the present invention.

FIG. 2C shows schematically a system for evaluating a surgical margin of tumor tissues of a living subject according to certain embodiments of the present invention. As shown in FIG. 2C, the system has similar elements with the system as shown in FIG. 2A.

FIGS. 3A and 3B show schematically two views of a system for evaluating a surgical margin of a specimen of a living subject according to certain embodiments of the present invention. As shown in FIG. 3A, the system 200 includes, among other things, a scanner and an optical probe 230. The scanner has a sample holder 246, two motors 241 and 242, two servomotors 243 and 244, and a camera 245. The motors 241 and 242 and their rotation directions are clearly shown on the FIG. 3A. The servomotor 243 is adapted to move the optical probe up (non-contact mode) and down (in contact mode for measurement). The mobile sample holder 246 is placed underneath the specimen 201 to hold the specimen 201 and to prevent the specimen 201 from sagging during measurement. The sample holder 246 can move up and down by activating the servomotor 244, and is in contact with the specimen 201 only during the measurement time. The camera 245, such as a webcam camera, is used in this prototype. The webcam captures images of the specimen 201 at different angles, allowing the 3D reconstruction of the specimen 201.

Figure 4:
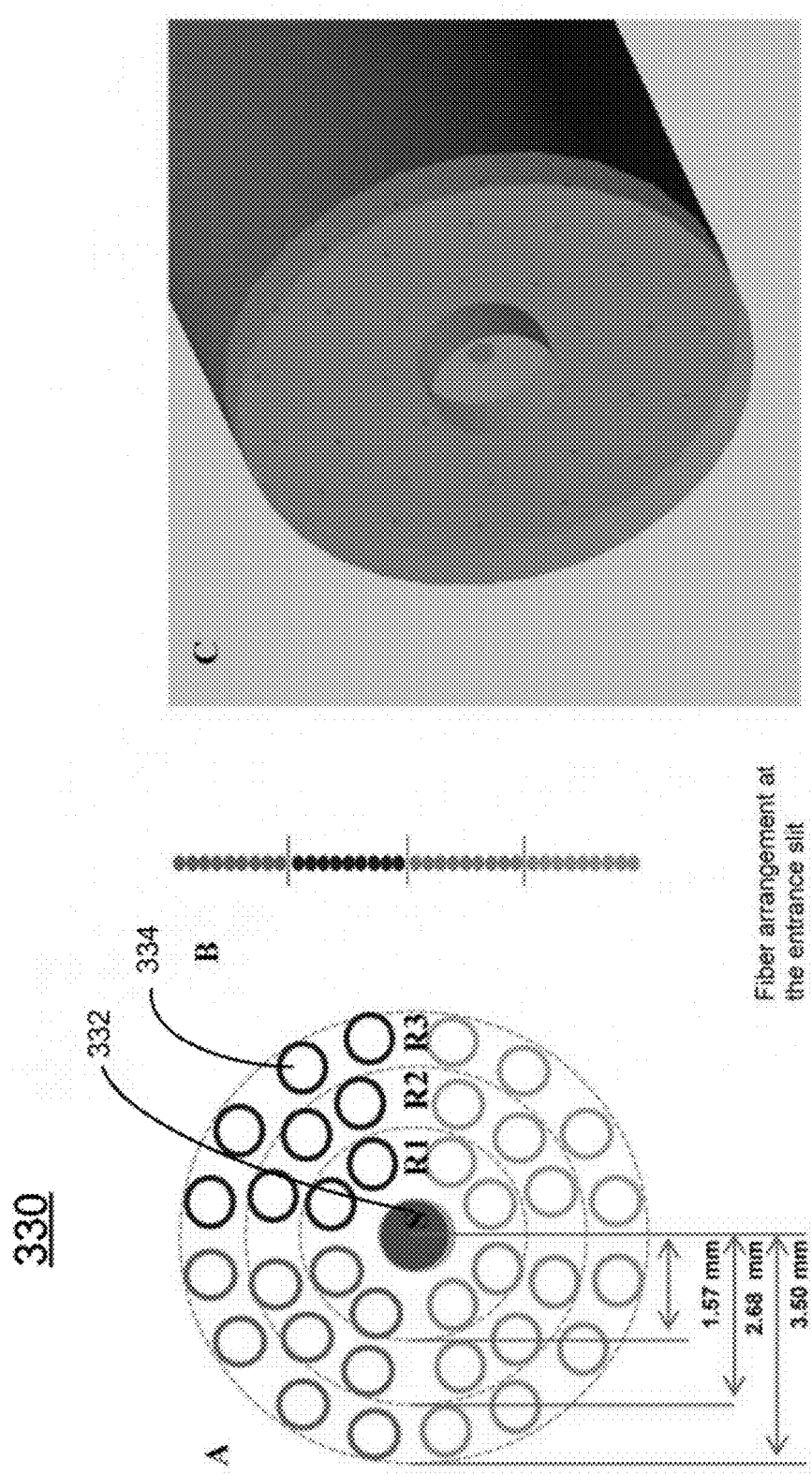
FIG. 4 shows schematically (A) a multi-fiber probe according to certain embodiments of the invention, (B) multi-fibers aligned at the entrance of the detector according to certain embodiments of the invention, and (C) a zoom view of the working end of the probe according to certain embodiments of the invention.

FIG. 4 shows schematically (A) a multi-fiber probe according to certain embodiments of the invention, (B) multi-fibers aligned at the entrance of the spectrometer according to certain embodiments of the invention, and (C) a zoom view of the working end of the probe according to certain embodiments of the invention. As shown in FIG. 4A, the optical probe 330 includes a plurality of optical fibers spatially arranged in a fiber array. In certain embodiments, the optical fibers include a source fiber 332 for delivering the source light emitted from the light source to the surface of the specimen, and a plurality of collection fibers 334 for collecting the diffused/reflected light generated from the interaction of the source light with the specimen. For the illustration purpose, the optical probe as shown in FIG. 4 uses the SORS technique and has the depth resolution of about 2 mm, optimized for breast margin evaluation.

The optical probe 330 as shown in FIG. 4 is an improved version of a previously developed optical probe (described in U.S. Publication No. 2010/0145200 A1). As shown in FIG. 4A, the optical probe 330 uses 36 fibers divided into 4 quadrants; each quadrant contains three rings. Each quadrant is similar in concept to the original probe built so that a total of 36 fibers is aligned at the entrance of the spectrometer as shown in FIG. 4B. The source fiber 332, which serves as the source of the optical probe 330, is positioned in a center of the fiber array. The collection fibers 334, which serve as the detectors of the optical probe 330, are positioned in the three rings having a center at the source fiber 332 such that each collection fiber 334 is offset from the source fiber 332. The main idea of the design of the optical probe 330 is to increase the number of collection fibers so that a larger area may be measured in a single integration, thus decreasing the number of measurements needed to cover the sample surface. FIG. 4C shows the fibers with inline filtering to reject fiber signal according to certain embodiments of the present invention.

Figure 5:
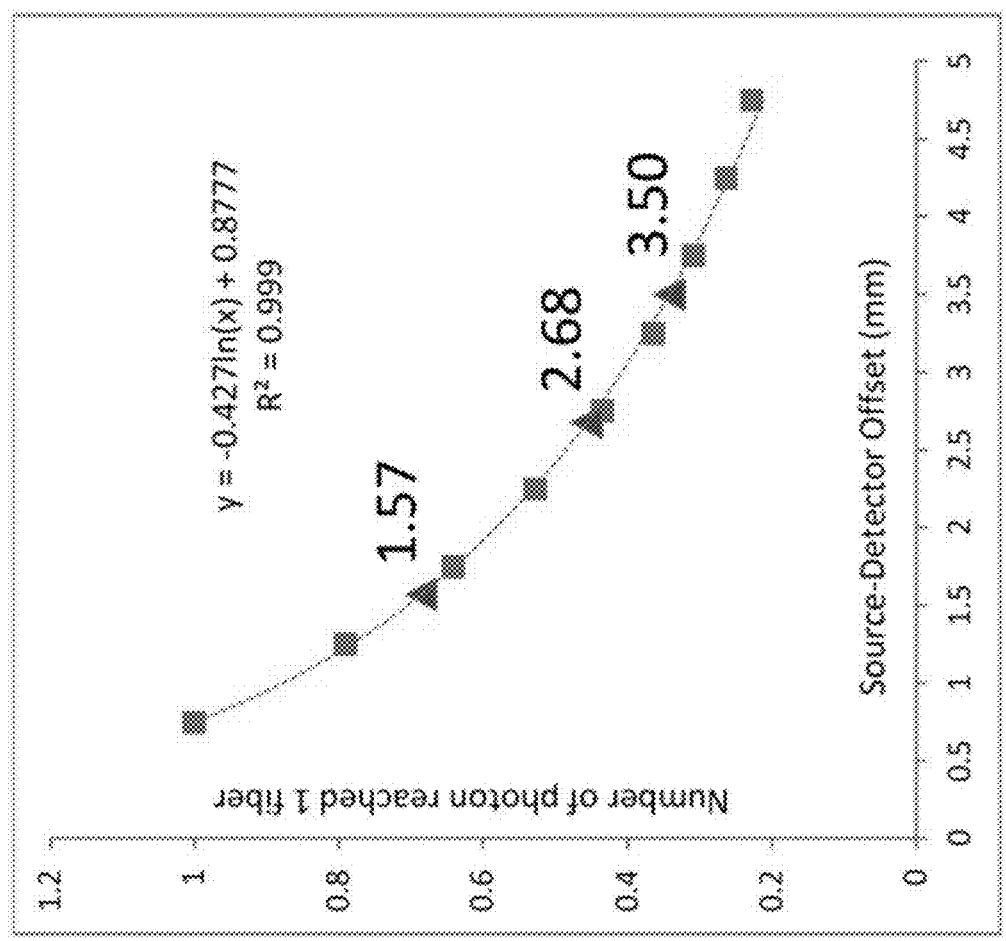
FIG. 5 shows the source-detector (S-D) offset for an equivalent S/N of the optical probe according to certain embodiments of the present invention.

FIG. 5 shows the source-detector (S-D) offset for an equivalent S/N of the optical probe according to certain embodiments of the present invention. The S-D offset represents the offset between the source (source fiber 332) and the detector (collection fibers 334) of each ring. The S-D offset of each ring is carefully calculated so that an equivalent S/N can be obtained, as shown in FIG. 5. For example, in the exemplary embodiment shown in FIG. 4A, the offset of the collection fibers in the first ring and the source fiber is about 1.57 mm; the offset of the collection fibers in the second ring and the source fiber is about 2.68 mm; and the offset of the collection fibers in the third ring and the source fiber is about 3.50 mm, respectively. In certain embodiments, Monte Carlo simulation was used to obtain the offset of FIG. 5 where the number of photons as a function of the S-D offset is shown. The square dots represent the simulation at different S-D and the blue curve represents the logarithm fitting curve. The triangles represent position of each ring allowing an equivalent number of photons to reach each ring according to certain embodiments of the present invention.

Figure 6:
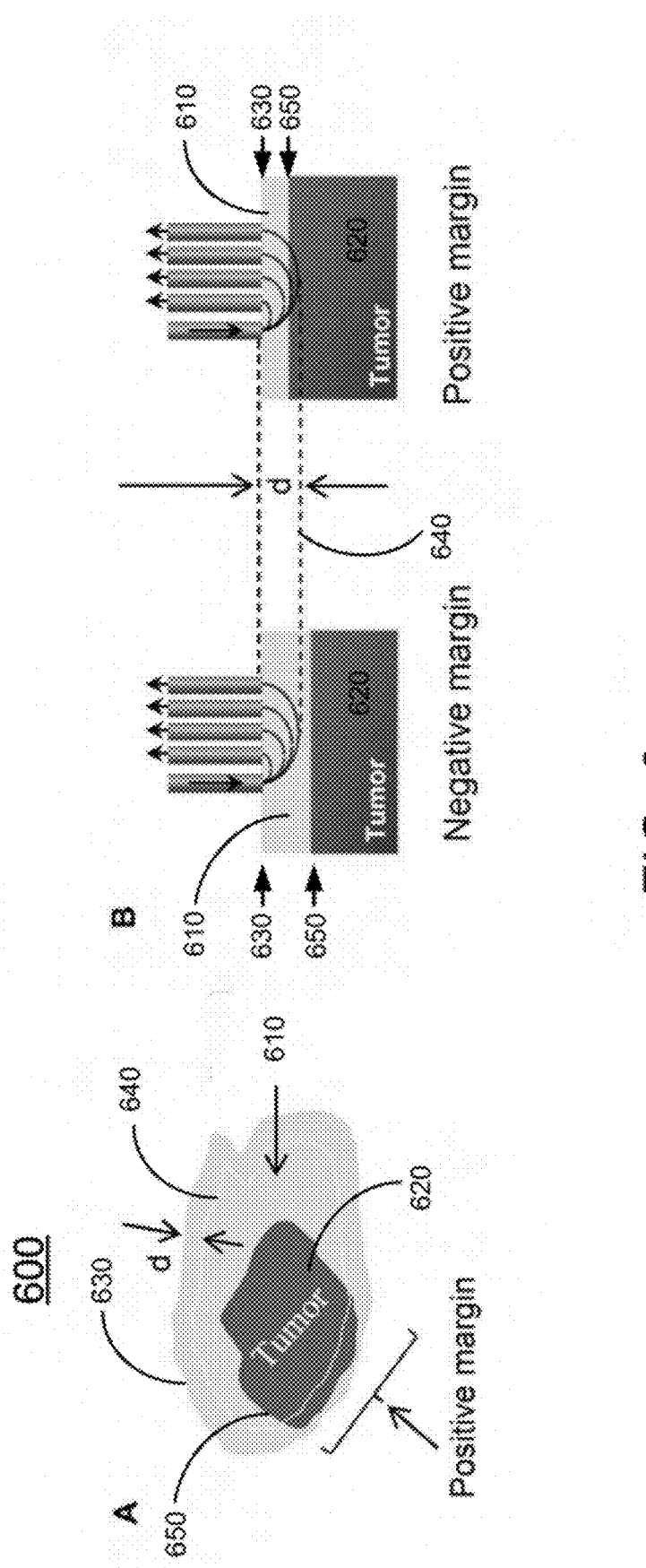
FIG. 6 shows schematically (A) a breast resected specimen according to certain embodiments of the present invention, and (B) tumor positive margins and negative margins according to certain embodiments of the present invention.

FIG. 6 shows schematically (A) a breast resected specimen according to certain embodiments of the present invention, and (B) tumor positive margins and negative margins according to certain embodiments of the present invention. As shown in FIG. 6A, the specimen 600 includes a normal tissue 610 and a tumor tissue 620. The outer boundary of the specimen 600 is the surgical margin 630, and the boundary between the normal tissue 610 and the tumor tissue 620 is the actual tumor boundary 650. A hypothesis tumor boundary 640 is predetermined to have a predetermined distance d inward from the surgical margin 630. In other words, the predetermined distance d exists between the surgical margin 630 and the hypothesis tumor boundary 640. At different positions of the specimen 600, the predetermined distance d may be longer or shorter than the actual distance between the surgical margin 630 and the actual tumor boundary 650. As shown in FIG. 6B, a positive margin exists when the predetermined distance d is longer than the actual distance between the surgical margin and the actual tumor boundary, and a negative margin exists when the predetermined distance d is shorter than the actual distance between the surgical margin and the actual tumor boundary.

In the previous patent application of U.S. Publication No. 2010/0145200 A1, the feasibility of using spatially offset Raman spectroscopy (SORS) to evaluate margin status on intact breast specimens has been demonstrated. The principle of the SORS method in evaluation of the margin is shown on FIG. 6B. For this technique to become standard operating room practice, simultaneous or sequential measurements of the entire tissue surface will be required.

Figure 7:
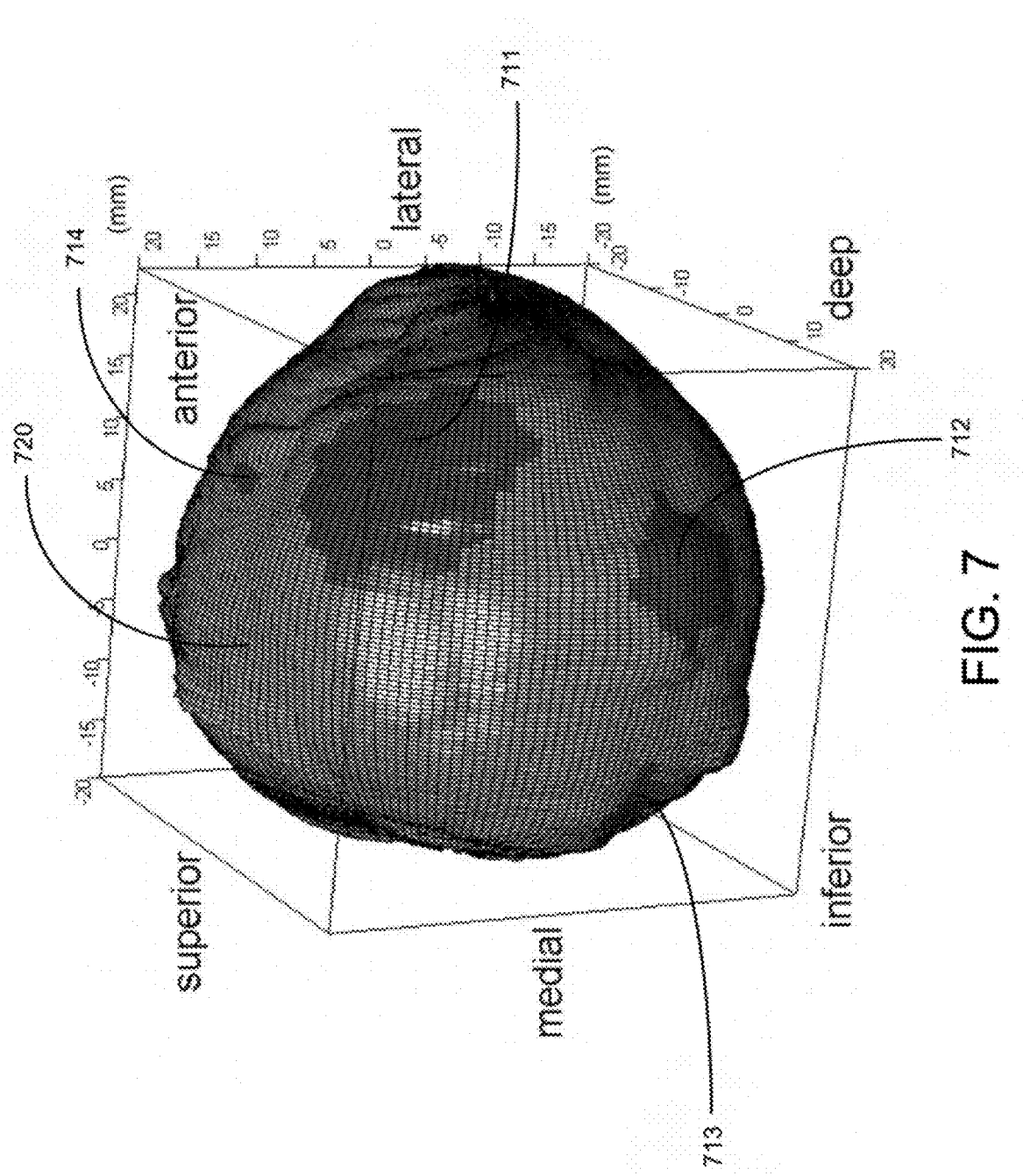
FIG. 7 shows the margin status of a phantom sample that mimics an excised cancer tumor according to certain embodiments of the present invention.

FIG. 7 shows the margin status of a phantom sample that mimics an excised cancer tumor according to one embodiment of the invention. As shown in FIG. 7, the sphere-shaped phantom sample has four regions that have different biological components in its margin. The sample is mounted on the scanner and the whole surface is automatically measured. Based on the spectrum recorded at each location, a classification method basing on principal component analysis algorithm, automatically evaluates if the margin status at that point is either positive or negative.

As can be seen in FIG. 7, the four regions 711-714, marked in red, correspond to four positive margin locations exactly detected and located. The green regions 720 correspond to the safe margin regions. The morphology of the sample is correctly reconstructed. This example demonstrates the capacity of the system to perform margin assessment for the entire sample surface. Highly detailed images of the margin status can be obtained and illustrated in a manner that the surgeon can easily recognize the exact location of any detected positive margin.

Light based methods have the potential to provide automated, fast determination of tumor cells in the tumor bed while the patient is still in the operating room without removing any tissue for such analysis. In certain embodiments, an intraoperative device using Raman spectroscopy and fluorescence spectroscopy is presented.

Fluorescence Spectroscopy

Intrinsic fluorescence (or autofluorescence) results from natural biological fluorophores such as flavins, porphyrins, collagen, elastin, and nicotinamide adenine dinucleotide (NAD). Autofluorescence spectra have been shown to differ between normal and neoplastic tissues in various organ systems possibly due to changes in fluorophore concentration or environment with the progression of disease [7]. Studies which exploit autofluorescence differences for tissue discrimination have been carried out for the brain [8-11], bronchus [12], colon [13], cervix [14], bladder [15], esophagus [16], skin [17], breast [18], and arterial wall [19]. Recently, fluorescence spectral imaging was also used to evaluate the status of breast surgical margins with a classification accuracy 85% sensitivity [20].

Raman Spectroscopy

Raman spectroscopy is a technique that measures energy shifts of scattered light from a sample. When the sample is irradiated with light, while the majority of the photon will be scattered elastically, a small fraction is scattered inelastically, resulting in an energy shift from the incident light. A sample's Raman spectrum is a biochemical figure print of its molecular structural. Many biological molecules have distinguishable spectra, so that the biochemical composition of a tissue can be determined from its Raman spectrum. One particularly relevant biochemical change for cancer cells is an increase in the nucleic acid content concomitant with increased proliferation and genetic instability. This change, among others such as changes in glycogen and collagen, can be detected with Raman spectroscopy [21,22].

As with most of the optical methods, several research groups including the PI's mentor have exploited Raman spectroscopy for the diagnosis of disease in many organs, including the cervix [23,24], bladder and prostate [25], lung [26], skin [27,28], and GI tract [29-31]. Recently our laboratory has reported an in vitro study where Raman spectroscopy was employed to discriminate negative or positive margins of breast tissue samples with 95% sensitivity and 100% specificity [32,33].

Combination of Fluorescence Spectroscopy and Raman Spectroscopy

Although Raman and fluorescence are two distinct phenomena, they occur at the same time when a light is shone on the sample. The Raman and fluorescence signals of a sample can be simultaneously measured using the same instrument. In certain embodiments, the Raman and fluorescence signals may be obtained using non-invasive optical technique that reveals the biochemical makeup of tissues by measuring the vibrational effects of inelastic light scattering on chemical bonds. The Raman and fluorescence signals are sensitive to molecular composition and micro-environment, and are ideal for in situ clinical diagnosis because it is rapid, specific, and non-destructive.

In certain embodiments, evaluation may be performed by: obtaining a raw spectrum from the optical data; generating a fluorescence spectrum (FS) and a Raman spectrum (RS) from the raw spectrum; and determining the margin status according to the FS and the RS.

Figure 8:
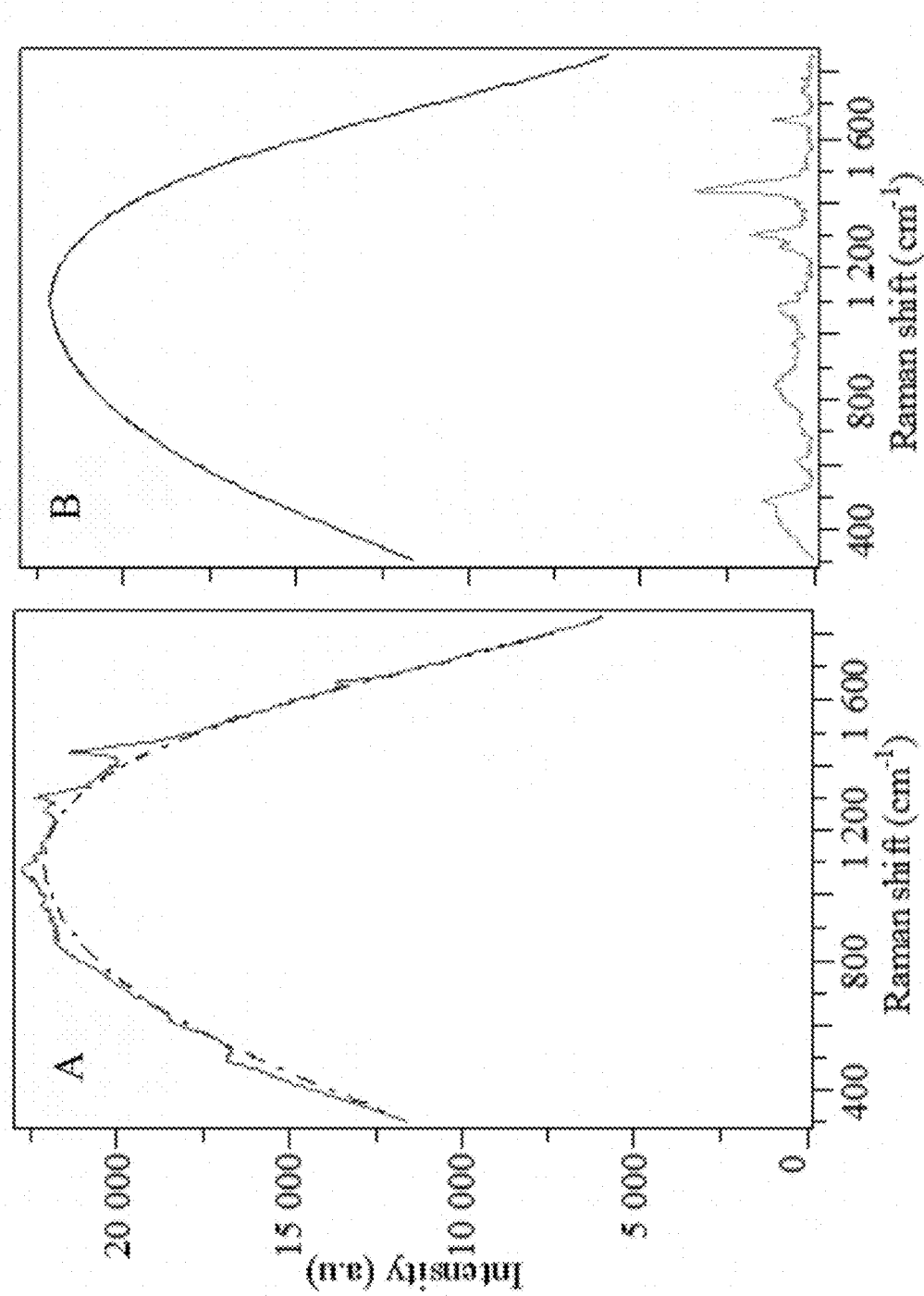
FIG. 8 shows the measured spectrums of a tissue sample according to certain embodiments of the present invention, wherein (A) shows a raw spectrum, and (B) shows a fluorescence spectrum (FS) and a Raman spectrum (RS) obtained from the raw spectrum of (A).

FIG. 8 shows the measured spectrums of a tissue sample according to certain embodiments of the present invention, wherein (A) shows a raw spectrum, and (B) shows a fluorescence spectrum (FS) and a Raman spectrum (RS) obtained from the raw spectrum of (A). As shown in FIG. 8A, the raw spectrum contains both Raman and fluorescence information. The fluorescence signal can be precisely approximated using a polynomial fitting (black dot curves under the spectrum in FIG. 8A and top curve on FIG. 8B). The Raman spectrum, which is obtained by subtracting the data of the raw spectrum from the fluorescence contribution, is shown on the bottom of FIG. 8B.

There have been some reports of Raman methods for STS differential diagnosis. For example, Manoharan et al. have identified features in Raman spectra that can be used to diagnosis liposarcoma from normal adipose tissue which can also be used to determine tumor grade [34]. Kast et al. have used Raman spectroscopy to differentiate rhabdomyosarcoma, Ewing sarcoma, neuroblastoma, and non-Hodgkin's lymphoma with 100% accuracy [35]. Using exogenous fluorescence spectroscopy, Eward et al. have demonstrated the feasibility of assessment of large surfaces in the tumor beds in animals [36]. However, the use of potentially toxic exogenous fluorescent dyes makes this approach less practical and thus limits its impact.

In certain embodiments, the combination of RS and FS may be used to provide a complete assessment of the tumor bed after STS excision. Within seconds, the device can localize any tumor residual and report to the surgeon. The complete removal of the tumor is thus ensured; the need for a second operation is greatly reduced or eliminated.

In certain embodiments, evaluation may be performed by using fluorescence imaging with the camera (for example, the camera 145 as shown in FIG. 2B) and the Raman spectrum obtained with the optical probe. In this case, the evaluation may be performed by: obtaining a raw spectrum from the optical data; generating a Raman spectrum (RS) from the raw spectrum; generating a fluorescence image (FI) from the images acquired by the camera; and determining the margin status according to the FI and the RS.

One aspect of the present invention relates the use of emerging proven methods to a new field of clinical challenge. No other group, to the best of applicant's knowledge, has applied Raman spectroscopy and intrinsic fluorescence spectroscopy to assess the tumor bed after soft tissue sarcoma excision. All the above mentioned works focus on using RS in differentiate several STS tissue types or using exogenous FS in assessing the tumor bed, with prior intravenous injection of fluorescent dyes. The combination of RS and FS proposed here could offer significant improvements over conventional approaches.

In addition, a further aspect of the invention relates to software implementation (i.e., computer executable instruction codes) stored in a non-transitory computer-readable medium which, when executed by a processor, cause a system to perform a method for evaluating a surgical margin of a specimen of a living subject. In certain embodiments, the software may be written in Labview and Matlab to perform the following tasks:

(1) Reconstructing the 3D morphology of the sample;
(2) Controlling of the scanner so that the entire sample surface can be automatically measured;
(3) Evaluating the margin status based on the presence of a cancer signal in spectra recorded at each location; and
(4) Displaying the margin status in 3D with morphological orientations.

In one embodiment, a system to perform the method includes a plurality of parts, which are listed in Table 1.

TABLE 1 parts used to construct the system

| Number | Part | Quantity | Utility |
| --- | --- | --- | --- |
| 1 | Motor | 2 | Move the sample and optical probes |
| 2 | Servomotor | 4 | Move the probes and sample holder |
| 3 | Electronic Board | 2 | Control the motors and servomotors |
| 4 | Camera | ≥1 | Take images of the specimen |
| 5 | Optical probes | ≥1 | Measure optical signal from the specimen |
| 6 | Spectrometer and Detector | ≥1 | Analyze the optical signal |
| 7 | PC and Software | 1 | Control measurements and analyze data |

Figure 9:
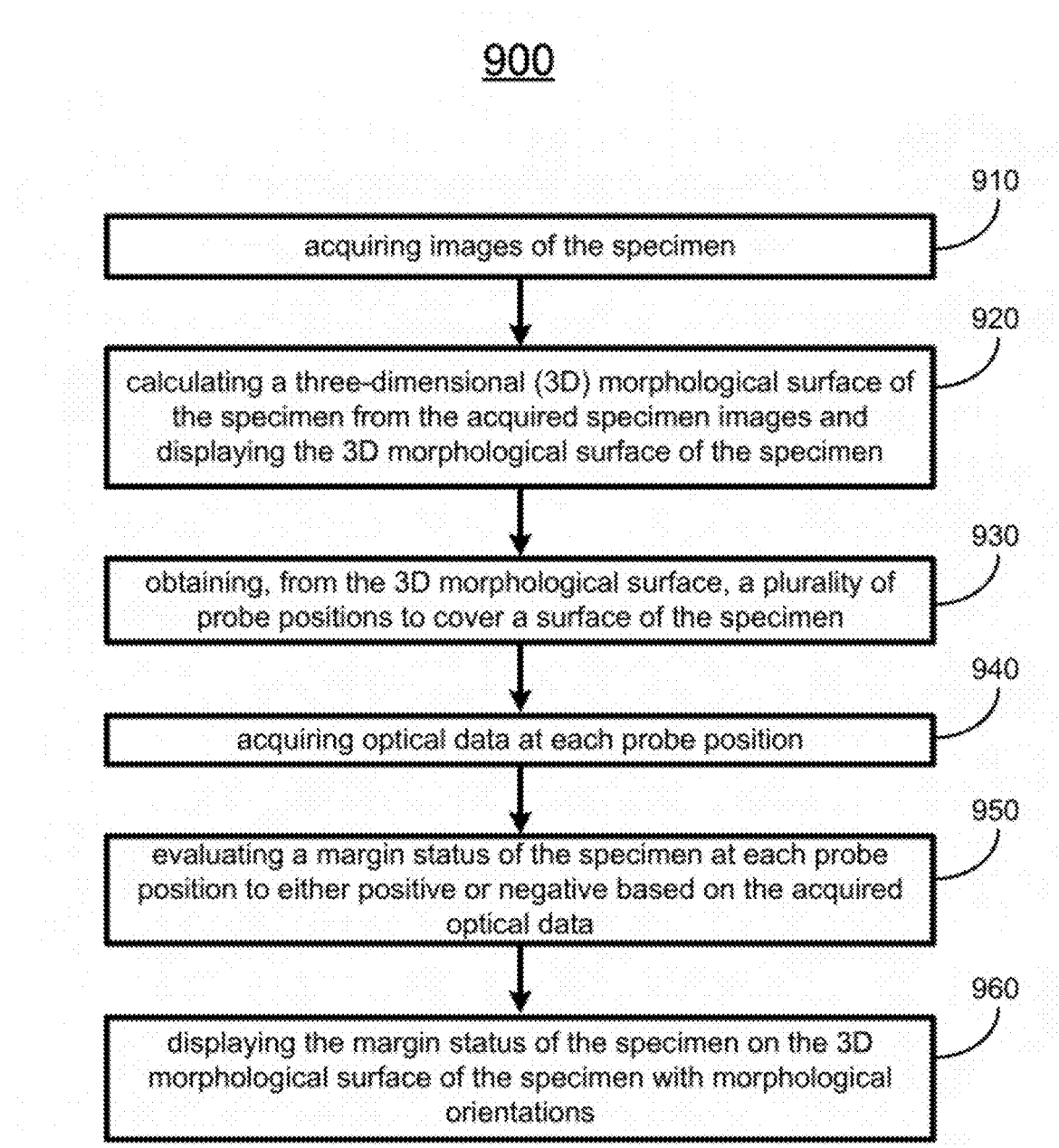
FIG. 9 shows a flowchart of a method of evaluating a surgical margin of a specimen of a living subject according to certain embodiments of the present invention.

Referring to FIG. 9, a flowchart 900 of a method for evaluating a surgical margin of a specimen of a living subject is shown according to one embodiment of the invention. The method includes the following steps: at step 910, images of the specimen are acquired. At step 920, a 3D morphological surface of the specimen is calculated from the acquired specimen images, and the 3D morphological surface of the specimen is displayed. At step 930, specimen locations are obtained from the 3D morphological surface to cover the entire surface of the specimen.

At step 940, optical data is acquired at each specimen location. In one embodiment, the acquiring step includes providing a source light; delivering the source light at each specimen location onto a surface of the specimen; and collecting diffused/reflected light generated from interaction of the source light with the specimen at the specimen location. In addition, the acquiring step is performed with at least one optical probe. In one embodiment, each optical probe includes a plurality of optical fibers spatially arranged in a fiber array. In certain embodiments, for each optical probe, the optical fibers include a source fiber for delivering the source light emitted from the light source to the surface of the specimen, and a plurality of collection fibers for collecting the diffused/reflected light generated from the interaction of the source light with the specimen. In certain embodiments, the source fiber is positioned in a center of the fiber array, and the plurality of collection fibers is positioned in one or more rings having a center at the source fiber such that each collection fiber is offset from the source fiber, as shown in FIG. 4.

Then, at step 950, a margin status of the specimen at each specimen location is evaluated to either positive or negative based on the acquired optical data. In certain embodiments, the evaluating step may be performed by: obtaining a raw spectrum, as shown in FIG. 8A, from the optical data; generating a fluorescence spectrum (FS) and a Raman spectrum (RS), as shown in FIG. 8B, from the raw spectrum; and determining the margin status according to the FS and the RS.

Finally, at step 960, the margin status of the specimen on the 3D morphological surface of the specimen with morphological orientations is displayed.

Additionally, the method may further include cooperatively moving the specimen and the at least one optical probe to acquire the optical data at all of the specimen locations to cover the entire surface of the specimen.

In certain embodiments, the method may further include: mounting the specimen in a scanner; and calibrating a position of the specimen in the scanner. In certain embodiments, the scanner includes: a sample holder for holding the specimen; a first motor for rotating the specimen along a first horizontal axis; and a second motor for moving the at least one optical probe along a surface of the specimen.

In certain embodiments, the steps 910-960 are all automatically performed by the software. However, manual intervention is needed at the beginning, in which the sample is mounted in the sample holder and the position of the sample is calibrated.

One aspect of the present invention relates to a non-transitory computer-readable medium storing computer executable instructions which, when executed by a processor, cause a system to perform a method for evaluating a surgical margin of tumor tissues of a living subject. In certain embodiments, the method performed by the system may be the method as disclosed in the flowchart of FIG. 9.

Example One

In this example, in vitro study is performed. Preliminary Raman and fluorescence spectra have been acquired to (1) demonstrate the ability of Raman and fluorescence spectroscopy in differentiating STS and normal tissues and (2) confirm the feasibility of measuring Raman and fluorescence signal of tumor beds in the operating room.

Under VU IRB approval (#120813), tumor and control samples from 20 patients have been acquired from the VU Cooperative Human Tissue Network. Raman spectra of the samples were collected using a portable fiber optic system, yielding 44 spectra from tumors and 33 spectra from control muscles.

Figure 10A:
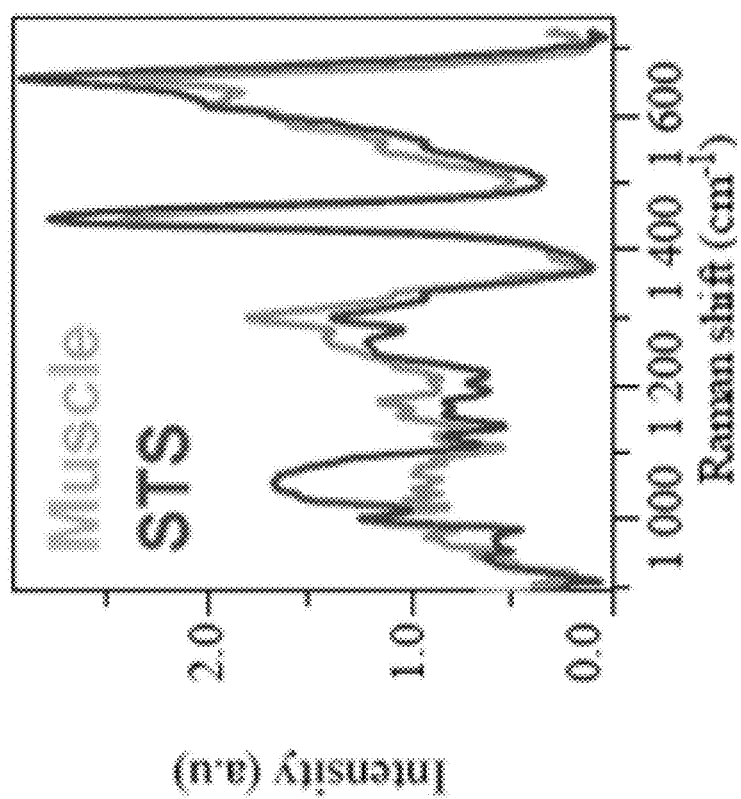
FIG. 10A shows schematically average Raman spectra of control muscle and STS samples according to certain embodiments of the present invention.

FIG. 10A shows schematically average Raman spectra of control muscle and STS samples according to certain embodiments of the present invention. Multivariate statistical analysis was used to classify spectra into tumor and control groups with 100% sensitivity and 100% specificity, as shown in Table 2.

TABLE 2

| Classification matrix for in vitro specimens | | | | | |
|---|---|---|---|---|---|
| | | Muscle | Tumor | | |
| Histopathology | Tumor | 0 | 44 | Sensitivity: | 100% |
| | Muscle | 32 | 0 | Specificity: | 100% |

Figure 10B:
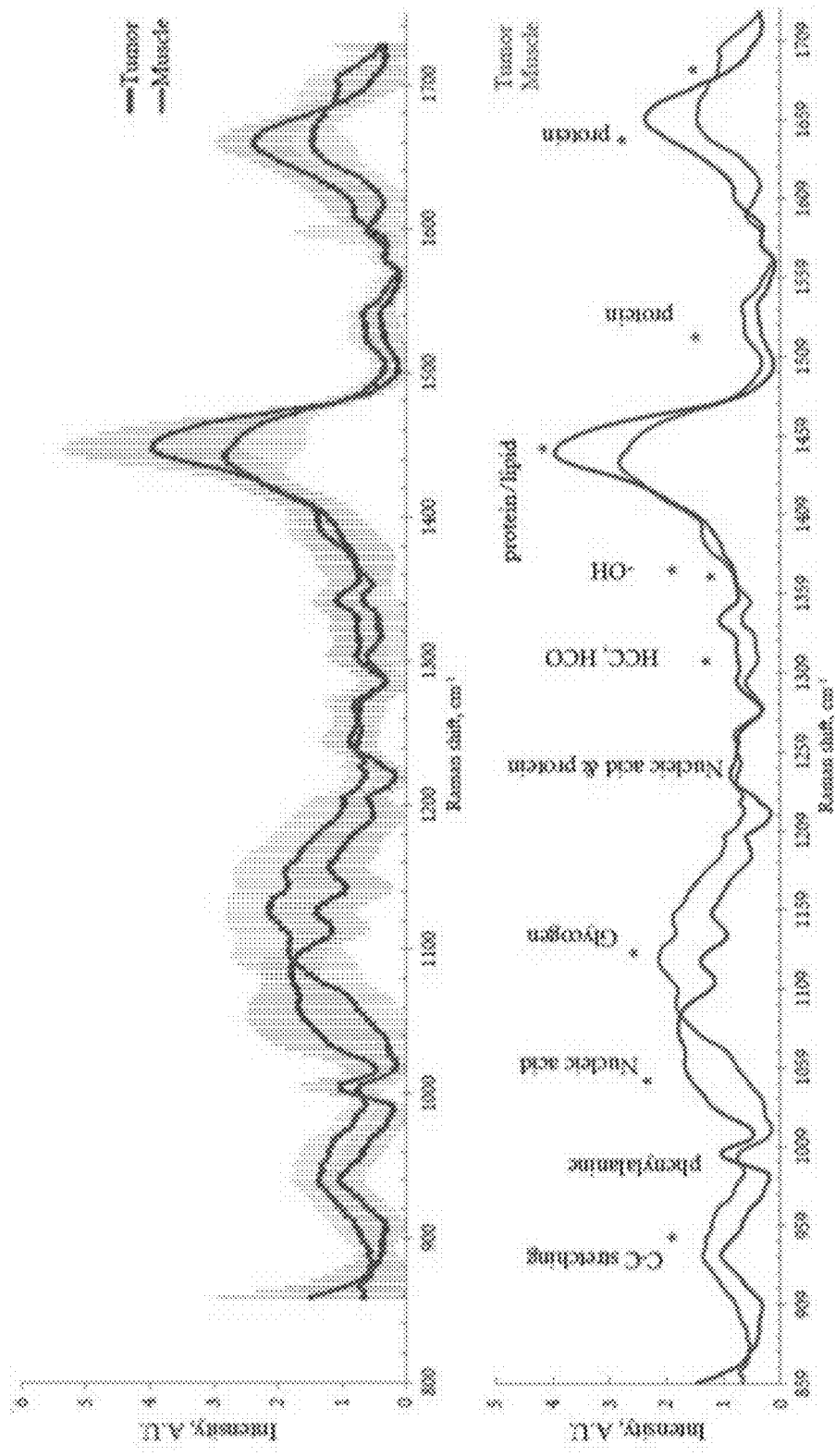
FIG. 10B shows schematically mean Raman spectra and associated biochemical peaks according to certain embodiments of the present invention.

FIG. 10B shows schematically mean Raman spectra and associated biochemical peaks according to certain embodiments of the present invention. As shown in FIG. 10B, statistical significance is indicated by asterisks (*: p<0.01; **: p<0.5).

Figure 11:
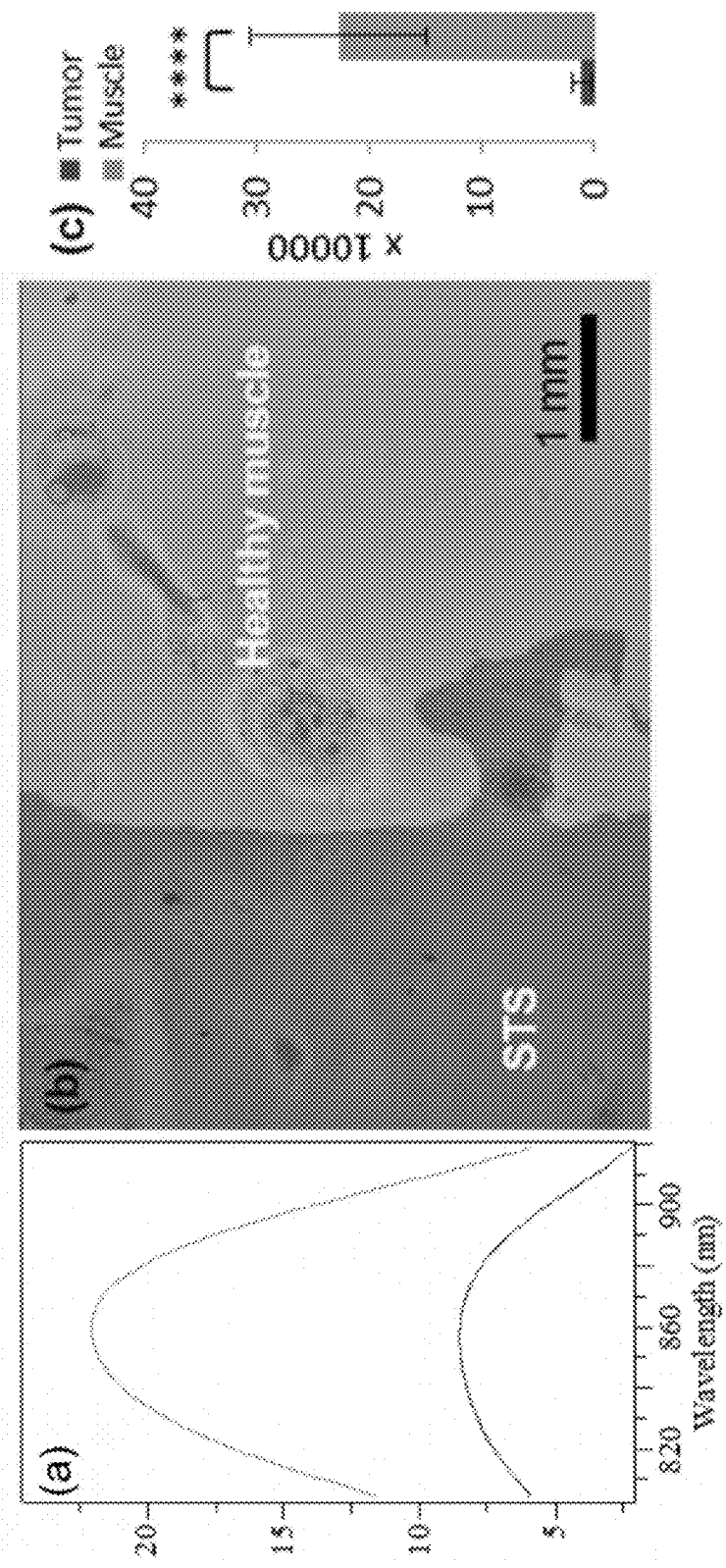
FIG. 11 shows (a) fluorescence spectra of muscle and STS, (b) an image of the surface of a samples and the boundary of STS and normal muscle, and (c) fluorescence intensity (mean±standard deviation) of the two regions according to certain embodiments of the present invention.

The in vitro data also suggest that FS can be used to differentiate muscle and STS. FIG. 11 shows (a) fluorescence spectra of muscle and STS, (b) an image of the surface of a samples and the boundary of STS and normal muscle, and (c) fluorescence intensity (mean±standard deviation) of the two regions according to certain embodiments of the present invention. As shown in FIG. 11(*a*), the fluorescent spectrum of healthy muscle and STS sample, measured under the same settings. It can be seen that muscle exhibits a much stronger fluorescence signal. As shown in FIG. 11(*b*), a tissue sample consists of healthy muscle on the right side, and STS on the left side, is used to demonstrated the feasibility of using fluorescence imaging to differentiate STS and muscle. A two dimensional map (~5 mm×3 mm) of the sample is measured and at each point on the surface, a spectrum is acquired. The data is processed and fluorescence information is extracted. Based on the fluorescence intensity, a threshold has been chosen to classify the sample into two regions, corresponding to tumor (red) and muscle (green). As shown in FIG. 11(*c*), the fluorescence intensity of those two regions is statistically different (p<0.0001). The border of STS and muscle is demarcated by the red curve in FIG. 11(*b*) and is confirmed histologically.

Figure 12:
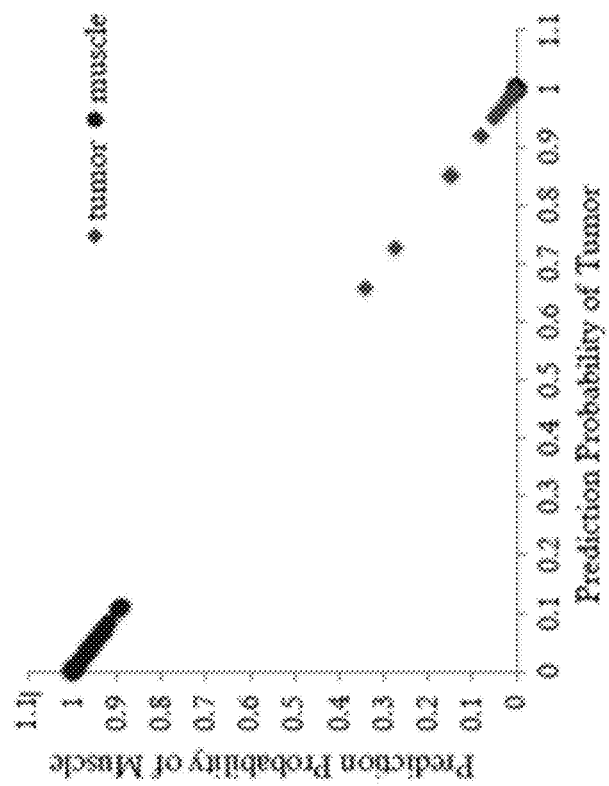
FIG. 12 shows the probability of individual samples being either normal muscle or tumor muscle according to certain embodiments of the present invention.

FIG. 12 shows the probability of individual samples being either normal muscle or tumor muscle according to certain embodiments of the present invention. These results suggest the potential of Raman and fluorescence spectroscopy in differentiating soft tissue sarcomas and healthy muscle with 100% accuracy.

Example Two

In this example, pilot clinical study is performed. The initial work demonstrated the feasibility of using Raman and fluorescence spectroscopy to differentiate STS and muscle on intact specimens in a laboratory setting. Studies are currently underway using the same approach in a clinical setting, and results are equally promising. Raman spectra were recorded for 3-10 seconds from multiple sites in the tumor bed of 19 patients undergoing STS excision at the VU Medical Center.

Figure 13:
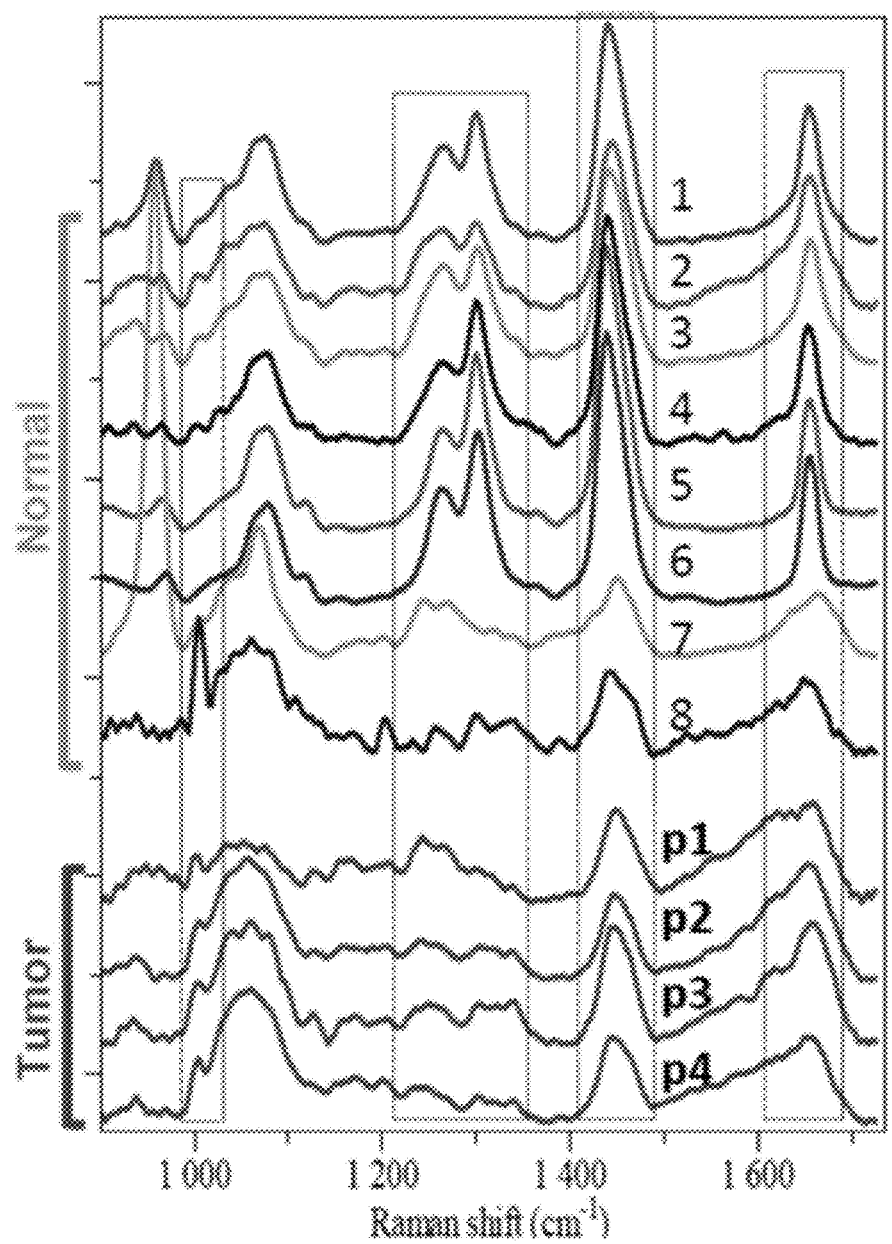
FIG. 13 shows schematically Raman spectra of in vivo tissues according to certain embodiments of the present invention.

FIG. 13 shows schematically Raman spectra of in vivo tissues according to certain embodiments of the present invention. As shown in FIG. 13, spectrum from 1 to 8 is the Raman spectrum of healthy tissues, as data 1 represents synovium; data 2 represents tendon; data 3 represents skin; data 4 represents nerve; data 5 represents bone marrow; data 6 represents fat; data 7 represents bone; and data 8 represents muscle. The Raman spectra of STS tumors from selected 4 patients are marked as p1-4 and are histologically confirmed to be: p1—round cell sarcoma; p2—malignant peripheral nerve sheath tumor; p3—undifferentiated pleomorphic sarcoma; and p4—undetermined STS.

Based on direct visualization, Raman spectra of STS (p1-p4) look similar, but they are different from the healthy ones (spectrum from 1 to 8). The gray bands highlight the spectral regions subject to the most dramatic differences. These include the difference of the 1006 cm$^{-1}$ peak generally attributed to phenylalanine; a decreasing of the 1265 and 1303 cm$^{-1}$ peaks, which tends to indicate a change in protein content; and the increasing width of the amide I peak around 1656 cm$^{-1}$. These significant spectral differences indicate the feasibility of RS in differentiating STS from normal tissues. A total of 396 spectra acquired from those 19 patients (in which 304 from healthy tissues and 86 from tumor) are used as an input of a support vector machine (SVM) classification algorithm (C=10 and gamma=0.001). All 304 spectra from healthy tissues and 92 from STS were predicted to have the right diagnosis with excellent sensitivity (94.6%) and specificity (98.4%), as shown in Table 3.

TABLE 3

Classification matrix for in vivo specimens

| | | Normal | Tumor | |
|---|---|---|---|---|
| Histopathology | Tumor | 5 | 87 | Sensitivity: 94.6% |
| | Normal | 301 | 3 | Specificity: 98.4% |

Figure 14:
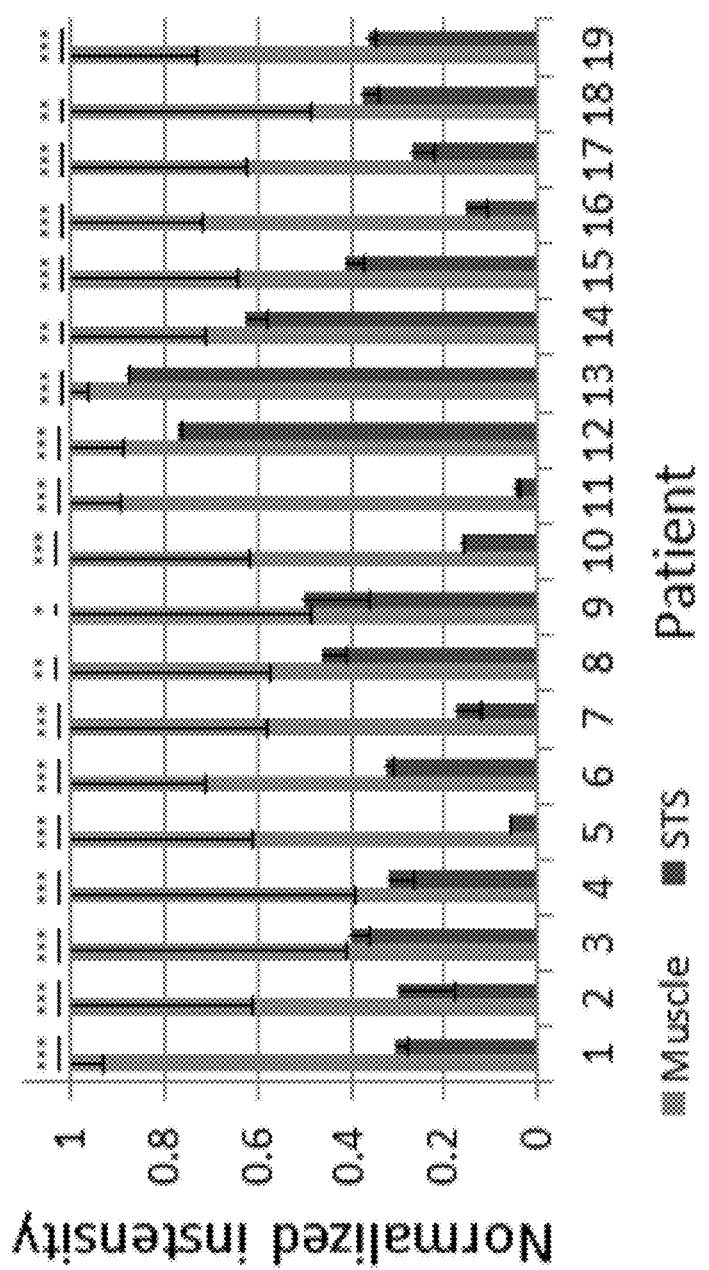
FIG. 14 shows Fluorescence intensity (mean±standard deviation) of muscle and tumor from 19 patients according to certain embodiments of the present invention.

The use of fluorescence spectroscopy in discriminating STS tumor and normal muscle is also evaluated. FIG. 14 shows fluorescence intensity (mean±standard deviation) of muscle and tumor from 19 patients according to certain embodiments of the present invention. As shown in FIG. 14, the fluorescence intensity of STS is found to be statistically smaller than that of the healthy muscle in all patients. These results indicate that fluorescence has the potential to be an excellent optical tool to locate STS in muscle tissues.

The preliminary results described above show the ability of Raman and fluorescence spectroscopy in differentiating STS from normal tissues with excellent sensitivity (94.6%) and specificity (98.4%). The pilot study also demonstrates the feasibility of acquiring good quality Raman and fluorescence data in clinical settings.

In sum, the present invention, among other things, recites methods and systems for evaluating surgical margins of tumor tissues of a living subject. In certain embodiments, Raman and fluorescence spectroscopy can be used to effectively discriminate between normal and tumor tissue during soft tissue sarcoma margin assessment.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE LIST

[1] American Cancer Society. Cancer Facts & Figures 2012. Atlanta: American Cancer Society, <http://www.cancer.org/acs/groups/content/@epidemiologysurveilance/documents/document/acspc-031941.pdf (2012).

[2] Atean, I. et al. Prognostic factors of extremity soft tissue sarcoma in adults. A single institutional analysis. Cancer/Radiothérapie 16, 661-666, doi:http://dx.doi.org/10.1016/j.canrad.2012.05.021 (2012).

[3] Blakely, M. L. et al. The impact of margin of resection on outcome in pediatric nonrhabdomyosarcoma soft tissue sarcoma. Journal of Pediatric Surgery 34, 672-675 (1999).

[4] Gronchi, A. et al. Status of Surgical Margins and Prognosis in Adult Soft Tissue Sarcomas of the Extremities: A Series of Patients Treated at a Single Institution. Journal of Clinical Oncology 23, 96-104, doi:10.1200/jco.2005.04.160 (2005).

[5] Grimer, R., Judson, I., Peake, D. & Seddon, B. Guidelines for the management of soft tissue sarcomas. Sarcoma 506182, 31 (2010).

[6] Gould, S. W. et al. Resection of soft tissue sarcomas with intra-operative magnetic resonance guidance. J Magn Reson Imaging 15, 114-119 (2002).

[7] Lakowicz, J. R. Principles of Fluorescence Spectroscopy. (Plenum Press, 1983).

[8] Lin, W. C., Toms, S. A., Motamedi, M., Jansen, E. D. & Mahadevan-Jansen, A. Brain tumor demarcation using optical spectroscopy; an in vitro study. J Biomed Opt 5, 214-220. (2000).

[9] Lin, W. C., Toms, S. A., Johnson, M., Jansen, E. D. & Mahadevan-Jansen, A. In vivo brain tumor demarcation using optical spectroscopy. Photochem Photobiol 73, 396-402. (2001).

[10] Chung, Y. G., Schwartz, J. A., Gardner, C. M., Sawaya, R. E. & Jacques, S. L. Diagnostic potential of laser-induced autofluorescence emission in brain tissue. J Korean Med Sci 12, 135-142. (1997).

[11] Bottiroli, G. et al. Brain tissue autofluorescence: an aid for intraoperative delineation of tumor resection margins. Cancer Detect Prev 22, 330-339 (1998).

[12] Zellweger, M. et al. In vivo autofluorescence spectroscopy of human bronchial tissue to optimize the detection and imaging of early cancers. J Biomed Opt 6, 41-51. (2001).

[13] Richards-Kortum, R. et al. Spectroscopic diagnosis of colonic dysplasia. Photochem Photobiol 53, 777-786. (1991).

[14] Ramanujam, N. et al. Cervical precancer detection using a multivariate statistical algorithm based on laser-induced fluorescence spectra at multiple excitation wavelengths. Photochem Photobiol 64, 720-735. (1996).

[15] D'Hallewin, M. A., Baert, L. & Vanherzeele, H. Fluorescence imaging of bladder cancer. Acta Urol Belg 62, 49-52. (1994).

[16] Panjehpour, M. et al. Spectroscopic diagnosis of esophageal cancer: new classification model, improved measurement system. Gastrointest Endosc 41, 577-581 (1995).

[17] Chwirot, B. W., Chwirot, S., Redzinski, J. & Michniewicz, Z. Detection of melanomas by digital imaging of spectrally resolved ultraviolet light-induced autofluorescence of human skin. *Eur J Cancer* 34, 1730-1734. (1998).

[18] Gupta, P. K., Majumder, S. K. & Uppal, A. Breast cancer diagnosis using N2 laser excited autofluorescence spectroscopy. *Lasers Surg Med* 21, 417-422 (1997).

[19] Warren, S. et al. Combined ultrasound and fluorescence spectroscopy for physico-chemical imaging of atherosclerosis. *IEEE Trans Biomed Eng* 42, 121-132. (1995).

[20] Keller, M. D. et al. BSuB6 (Optical Society of America).

[21] Mahadevan-Jansen, A. in *Raman Spectroscopy: From Benchtop to Bedside, Biomedical Photonics Handbook*, (ed 30:1-30:27 T. Vo-Dinh, CRC Press, Washington D.C., 2003.).

[22] Mahadevan-Jansen, A. & Richards-Kortum, R. R. Raman spectroscopy for the detection of cancers and precancers. *Journal of biomedical optics* 1, 31-70, doi:10.1117/12.227815 (1996).

[23] Mahadevan-Jansen, A. et al. Near-infrared Raman spectroscopy for in vitro detection of cervical precancers. *Photochem Photobiol* 68, 123-132 (1998).

[24] Mahadevan-Jansen, A., Mitchell, M. F., Ramanujam, N., Utzinger, U. & Richards-Kortum, R. Development of a fiber optic probe to measure NIR Raman spectra of cervical tissue in vivo. *Photochem Photobiol* 68, 427-431 (1998).

[25] Crow, P. et al. Assessment of fiberoptic near-infrared raman spectroscopy for diagnosis of bladder and prostate cancer. *Urology* 65, 1126-1130, doi:10.1016/j.urology.2004.12.058 (2005).

[26] Huang, Z. et al. Near-infrared Raman spectroscopy for optical diagnosis of lung cancer. *International journal of cancer. Journal international du cancer* 107, 1047-1052, doi:10.1002/ijc.11500 (2003).

[27] Lieber, C. A., Majumder, S. K., Ellis, D. L., Billheimer, D. D. & Mahadevan-Jansen, A. In vivo nonmelanoma skin cancer diagnosis using Raman microspectroscopy. *Lasers Surg Med* 40, 461-467 (2008).

[28] Sigurdsson, S. et al. Detection of skin cancer by classification of Raman spectra. *IEEE transactions on bio-medical engineering* 51, 1784-1793, doi:10.1109/TBME.2004.831538 (2004).

[29] Shetty, G., Kendall, C., Shepherd, N., Stone, N. & Barr, H. Raman spectroscopy: elucidation of biochemical changes in carcinogenesis of oesophagus. *British journal of cancer* 94, 1460-1464, doi:10.1038/sj.bjc.6603102 (2006).

[30] Shim, M. G., Song, L. M., Marcon, N. E. & Wilson, B. C. In vivo near-infrared Raman spectroscopy: demonstration of feasibility during clinical gastrointestinal endoscopy. *Photochem Photobiol* 72, 146-150 (2000).

[31] Molckovsky, A., Song, L. M., Shim, M. G., Marcon, N. E. & Wilson, B. C. Diagnostic potential of near-infrared Raman spectroscopy in the colon: differentiating adenomatous from hyperplastic polyps. *Gastrointestinal endoscopy* 57, 396-402, doi:10.1067/mge.2003.105 (2003).

[32] Keller, M. D. et al. Development of a spatially offset Raman spectroscopy probe for breast tumor surgical margin evaluation. *Journal of biomedical optics* 16, 077006, doi:10.1117/1.3600708 (2011).

[33] Mahadevan-Jansen A et al. Looking Below the Surface of Breast Tissue during Surgery. *Spectroscopy* (2011).

[34] Manoharan, R. et al. in *SPIE (Europe)*. 128-132 (Bellingham).

[35] Kast, R. et al. Differentiation of small round blue cell tumors using Raman spectroscopy. *Journal of Pediatric Surgery* 45, 1110-1114, doi:http://dx.doi.org/10.1016/j.jpedsurg.2010.02.072 (2010).

[36] Eward, W. et al. A Novel Imaging System Permits Real-time in Vivo Tumor Bed Assessment After Resection of Naturally Occurring Sarcomas in Dogs. *Clin Orthop Relat Res*, 1-9, doi:10.1007/s11999-012-2560-8 (2012).

What is claimed is:

1. A method of evaluating a surgical margin of tumor tissues of a living subject, comprising:
    (a) acquiring images of a specimen of the tumor tissues;
    (b) calculating a three-dimensional (3D) morphological surface of the specimen from the acquired images and displaying the 3D morphological surface;
    (c) obtaining, from the 3D morphological surface, a plurality of specimen locations to cover a surface of the specimen;
    (d) acquiring optical data at each specimen location by at least one optical probe, each optical probe comprising a source optical fiber delivering source light at each specimen location onto a surface of the specimen, and a plurality of collection optical fibers for collecting diffused/reflected light generated from interaction of the source light with the specimen at the specimen location;
    (e) evaluating a margin status of the specimen at each specimen location to either positive or negative based on the acquired optical data; and
    (f) displaying the margin status of the specimen on the 3D morphological surface of the specimen with morphological orientations,
        wherein the plurality of collection optical fibers is arranged in an array, wherein the plurality of collection optical fibers is divided into N groups, such that a first group of the collection optical fibers each is positioned away along a radial direction from the source optical fiber with a first spatial offset $R_1$ and a N-th group of the collection optical fibers each is positioned away along the radial direction from the source optical fiber with a N-th spatial offset $R_N$, wherein N is an positive integer, and $R_1 \leq R_2 \leq \ldots \leq R_{N-1} \leq R_N$; and
        wherein the tumor tissues include breast cancer tissues, N=3, $R_1$=1.57 mm, $R_2$=2.68 mm, and $R_3$=3.50 mm.

2. The method of claim 1, further comprising:
    cooperatively moving the specimen and the at least one optical probe to acquire the optical data at all of the specimen locations.

3. The method of claim 1, further comprising:
    mounting the specimen in a scanner; and
    calibrating a position of the specimen in the scanner.

4. The method of claim 3, wherein the scanner comprises:
    a first motor for rotating the specimen along a first horizontal axis; and
    a second motor for moving the at least one optical probe along a surface of the specimen.

5. The method of claim 4, wherein the scanner further comprises a camera for acquiring images of the specimen so as to reconstruct a three-dimensional (3D) morphological surface of the specimen.

6. The method of claim 5, wherein the evaluating step comprises:
   obtaining a raw spectrum from the optical data;
   generating a Raman spectrum (RS) from the raw spectrum; and
   determining the margin status according to the RS.

7. The method of claim 5, wherein the evaluating step comprises:
   generating a fluorescence signal from the images acquired by the camera; and
   determining the margin status according to the fluorescence signal.

8. The method of claim 1, wherein the evaluating step comprises:
   obtaining a raw spectrum from the optical data;
   generating a fluorescence spectrum (FS) and a Raman spectrum (RS) from the raw spectrum; and
   determining the margin status according to the FS and the RS.

9. A non-transitory computer-readable medium storing computer executable instructions which, when executed by a processor, cause a system to perform a method for evaluating a surgical margin of tumor tissues of a living subject, the method comprising:
   (a) acquiring images of a specimen of the tumor tissues;
   (b) calculating a three-dimensional (3D) morphological surface of the specimen from the acquired images and displaying the 3D morphological surface;
   (c) obtaining, from the 3D morphological surface, a plurality of specimen locations to cover a surface of the specimen;
   (d) acquiring optical data at each specimen location by at least one optical probe, each optical probe comprising a source optical fiber delivering source light at each specimen location onto a surface of the specimen, and a plurality of collection optical fibers for collecting diffused/reflected light generated from interaction of the source light with the specimen at the specimen location;
   (e) evaluating a margin status of the specimen at each specimen location to either positive or negative based on the acquired optical data; and
   (f) displaying the margin status of the specimen on the 3D morphological surface of the specimen with morphological orientations,
   wherein the plurality of collection optical fibers is arranged in an array, wherein the plurality of collection optical fibers is divided into N groups, such that a first group of the collection optical fibers each is positioned away along a radial direction from the source optical fiber with a first spatial offset $R_1$ and a N-th group of the collection optical fibers each is positioned away along the radial direction from the source optical fiber with a N-th spatial offset $R_N$, wherein N is an positive integer, and $R_1 \leq R_2 \leq \ldots \leq R_{N-1} \leq R_N$; and
   wherein the tumor tissues include breast cancer tissues, N=3, $R_1$=1.57 mm, $R_2$=2.68 mm, and $R_3$=3.50 mm.

10. The non-transitory computer-readable medium of claim 9, wherein the method further comprises cooperatively moving the specimen and the at least one optical probe to acquire the optical data at all of the specimen locations.

11. The non-transitory computer-readable medium of claim 9, wherein the evaluating step comprises:
    obtaining a raw spectrum from the optical data;
    generating a fluorescence spectrum (FS) and a Raman spectrum (RS) from the raw spectrum; and
    determining the margin status according to the FS and the RS.

12. The non-transitory computer-readable medium of claim 9, wherein the method further comprises:
    mounting the specimen in a scanner; and
    calibrating a position of the specimen in the scanner.

13. The non-transitory computer-readable medium of claim 12, wherein the scanner comprises a camera for acquiring images of the specimen so as to reconstruct a three-dimensional (3D) morphological surface of the specimen.

14. The non-transitory computer-readable medium of claim 13, wherein the evaluating step comprises:
    obtaining a raw spectrum from the optical data;
    generating a Raman spectrum (RS) from the raw spectrum; and
    determining the margin status according to the RS.

15. The non-transitory computer-readable medium of claim 13, wherein the evaluating step comprises:
    generating a fluorescence signal from the images acquired by the camera; and
    determining the margin status according to the fluorescence signal.

* * * * *